US012748114B2

(12) United States Patent
Wands et al.

(10) Patent No.: US 12,748,114 B2
(45) Date of Patent: Sep. 29, 2026

(54) DIAGNOSIS, PROGNOSIS AND TREATMENT OF MALIGNANT NEOPLASMS

(71) Applicant: Rhode Island Hospital, Providence, RI (US)

(72) Inventors: Jack R. Wands, Warwick, RI (US); Rolf I. Carlson, Westwood, MA (US); Xiaoqun Dong, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 18/998,119

(22) PCT Filed: Jul. 25, 2023

(86) PCT No.: PCT/US2023/070963

§ 371 (c)(1),
(2) Date: Jan. 23, 2025

(87) PCT Pub. No.: WO2024/026318

PCT Pub. Date: Feb. 1, 2024

(65) Prior Publication Data

US 2025/0264470 A1 Aug. 21, 2025

Related U.S. Application Data

(60) Provisional application No. 63/369,332, filed on Jul. 25, 2022.

(51) Int. Cl.

*G01N 33/573* (2006.01)
*C07K 16/40* (2006.01)
*G01N 33/575* (2026.01)

(52) U.S. Cl.

CPC ........... *G01N 33/573* (2013.01); *C07K 16/40* (2013.01); *C12Y 114/11016* (2013.01); *G01N 33/57585* (2026.01); *C07K 2317/24* (2013.01); *G01N 2333/90245* (2013.01)

(58) Field of Classification Search

None
See application file for complete search history.

(56) References Cited

U.S. PATENT DOCUMENTS

| | | | |
|---|---|---|---|
| 6,797,696 B2 | 9/2004 | Wands et al. |
| 7,094,556 B2 | 8/2006 | Wands et al. |
| 2005/0123545 A1 | 6/2005 | Wands et al. |
| 2021/0317208 A1 | 10/2021 | Culp et al. |
| 2022/0162341 A1 | 5/2022 | Olsen |

FOREIGN PATENT DOCUMENTS

| | | | |
|---|---|---|---|
| CN | 1905898 A | 1/2007 |
| WO | 2012104824 A1 | 8/2012 |
| WO | 2019040537 A1 | 2/2019 |
| WO | 2019041036 A1 | 3/2019 |
| WO | 2019246093 A1 | 12/2019 |

OTHER PUBLICATIONS

Kussie "A Single Engineered Amino Acid Substitution Changes Antibody Fine Specificity" J immunol 152(1):146-52 (Year: 1994).*

Chen "Enhancement and destruction of antibody function by somatic mutation: unequal occurrence is controlled by V gene combinatorial associations" EMBO 14(12):2784-2794 (Year: 1995).*

"International Search Report and Written Opinion received for PCT Patent Application No. PCT/US2023/070963, mailed on Mar. 1, 2024", 14 pages.

Aihara, et al., "A Cell-Surface β-Hydroxylase Is a Biomarker and Therapeutic Target for Hepatocellular Carcinoma", Hepatology, vol. 60, No. 4, Oct. 2014, pp. 1302-1313.

Berend, et al., "Association between Ratio of Matrix Metalloproteinase-1 to Tissue Inhibitor of Metalloproteinase-1 and Local Recurrence, Metastasis, and Survival in Human Chondrosarcoma", The Journal of Bone and Joint Surgery, vol. 80-A, No. 1, Jan. 1998, pp. 11-17.

Dong, et al., "Aspartate β-Hydroxylase Expression Promotes a Malignant Pancreatic Cellular Phenotype", Oncotarget, vol. 6, No., 2, Nov. 26, 2014, pp. 1231-1248.

Elvidge, et al., "Concordant Regulation of Gene Expression by Hypoxia and 2-Oxoglutarate-Dependent Dioxygenase Inhibition: The Role of HIF-1α, HIF-2α, and Other Pathways", The Journal of Biological Chemistry, vol. 281, No. 22, Jun. 2, 2006, pp. 15215-15226.

Engin, et al., "Notch Signaling Contributes to the Pathogenesis of Human Osteosarcomas", Human Molecular Genetics, vol. 18, No. 8, Feb. 19, 2009, pp. 1464-1470.

Fang, et al., "Matrix Metalloproteinase-2 is Required for the Switch to the Angiogenic Phenotype in a Tumor Model", PNAS, vol. 97, No. 8, Apr. 11, 2000, pp. 3884-3889.

Hou, et al., "WISP-1 Increases MMP-2 Expression and Cell Motility in Human Chondrosarcoma Cells", Biochemical Pharmacology, vol. 81, 2011, pp. 1286-1295.

Huang, et al., "Anti-Tumor Effects of Second Generation β-hydroxylase Inhibitors on Cholangiocarcinoma Development and Progression", PLoS one, vol. 11, No. 3, Mar. 8, 2016, pp. 1-18.

Iwagami, et al., "Aspartate β-hydroxylase Modulates Cellular Senescence Through Glycogen Synthase Kinase 3beta in Hepatocellular Carcinoma", Hepatology, vol. 63, No. 4, Apr. 2016, pp. 1213-1226.

Jawad, et al., "Matrix Metalloproteinase 1: Role in Sarcoma Biology", PLoS One, vol. 5, Issue 12, Dec. 2010, pp. 1-11.

Jia, et al., "cDNA Cloning and Expression of Bovine Aspartyl (Asparaginyl) β-Hydroxylase", The Journal of Biological Chemistry, vol. 267, No. 20, Jul. 15, 1992, pp. 14322-14327.

Korioth, et al., "Cloning and Characterization of the Human Gene Encoding Aspartyl β-hydroxylase", Gene, vol. 150, 1994, pp. 395-399.

(Continued)

*Primary Examiner* — Adam Weidner

(74) *Attorney, Agent, or Firm* — Adler Pollock & Sheehan P.C.

(57) ABSTRACT

This disclosure relates to antibodies and derivatives that bind the full-length isoform of aspartate beta-hydroxylase (ASPH) and uses thereof. The antibodies and derivatives are useful in compositions and methods for detecting and/or treating a malignant neoplasm in a subject and for predicting subsequent complications of untreated progression of the malignant neoplasm in the subject.

8 Claims, 7 Drawing Sheets

Specification includes a Sequence Listing.

(56) References Cited

OTHER PUBLICATIONS

Lavaissiere, et al., "Overexpression of Human Aspartyl (Asparaginyl) β-Hydroxylase in Hepatocellular Carcinoma and Cholangiocarcinoma", The Journal of Clinical Investigation, vol. 98, No. 6, Sep. 1996, pp. 1313-1323.
Longato, et al., "Overexpression of Insulin Receptor Substrate-1 and Hepatitis Bx Genes Causes Premalignant Alterations in the Liver", Hepatology, vol. 49, No. 6, Jun. 2009, pp. 1935-1943.
Patel, et al., "Mutations in ASPH Cause Facial Dysmorphism, Lens Dislocation, Anterior-Segment Abnormalities, and Spontaneous Filtering Blebs, or Traboulsi Syndrome", The American Journal of Human Genetics, vol. 94, May 1, 2014, pp. 755-759.
Soderstrom, et al., "Expression of Matrix Metalloproteinases and Tissue Inhibitors of Metalloproteinases in Human Chondrosarcomas", APMIS, vol. 109, 2001, pp. 305-315.
Tang, et al., "IL-6 Increases MMP-13 Expression and Motility in Human Chondrosarcoma Cells", The Journal of Biological Chemistry, vol. 286, No. 13, Apr. 1, 2011, pp. 11056-11066.
Uria, et al., "Collagenase-3 (MMP-13) Expression in Chondrosarcoma Cells and Its Regulation by Basic Fibroblast Growth Factor", American Journal of Pathology, vol. 153, No. 1, Jul. 1998, pp. 91-101.
Xu, et al., "Metastasis-Associated Lung Adenocarcinoma Transcript I Promotes the Proliferation of Chondrosarcoma Cell via Activating Notch-I Signaling Pathway", OncoTargets and Therapy, vol. 9, 2016, pp. 2143-2151.
Zhou, et al., "Prognostic Significance of Matrix Metalloproteinase 9 Expression in Osteosarcoma: A Meta-Analysis of 16 Studies", Medicine, vol. 97, No. 44, 2018, pp. 1-7.
"Extended European Search report received for EP Patent Application No. 23847510.7, mailed on Jul. 2, 2026", 10 pages.
Huyan, et al., "Development of a Novel Anti-Human Aspartyl-(Asparaginyl) β-Hydroxylase Monoclonal Antibody With Diagnostic and Therapeutic Potential", Oncology Letters, vol. 13, 2017, pp. 1539-1546.
Revskaya, et al., "A Radiolabeled Fully Human Antibody to Human Aspartyl (Asparaginyl) β-HHydroxylase Is a Promising Agent for Imaging and Therapy of Metastatic Breast Cancer", Cancer Biotherapy & Radiopharmaceuticals, vol. 32, No. 2, 2017, pp. 57-65.

* cited by examiner

Specimen-16

H&E x1000

ASPH x1000

DIAGNOSIS, PROGNOSIS AND TREATMENT OF MALIGNANT NEOPLASMS

CROSS-REFERENCE TO RELATED APPLICATIONS

This patent application is a national phase filing under 35 U.S.C. § 371 of International Application No. PCT/US2023/070963 filed Jul. 25, 2023, which claims priority under 35 U.S.C. § 119(e) to the provisional patent application U.S. Ser. No. 63/369,332, filed Jul. 25, 2022, the entire contents of which are hereby incorporated by reference herein.

FIELD OF THE INVENTION

This disclosure generally relates to a method for diagnosing and treating a malignant neoplasm in a mammal by contacting a malignant cell or a bodily fluid containing components derived from malignant cells of the mammal with an antibody which recognizes the full-length isoform of human aspartate β-hydroxylase (ASPH) (Gene ID: 444). Methods for treating a malignant neoplasm in a mammal with a monoclonal antibody (mAb) or its derivatives, such as a single-chain variable fragment (scFv) and a nanobody, which recognizes the full-length isoform of ASPH linked to a cytotoxic agent are also within the invention.

BRIEF DESCRIPTION OF THE SEQUENCE LISTING

The instant application contains a Sequence Listing which has been submitted electronically in XML form at and is hereby incorporated by reference in its entirety. Said XML copy, created on Dec. 4, 2023, is named RIH1363_405002-536N01US_SL.xml and is 25 KB (kilobytes) in size.

BACKGROUND OF THE INVENTION

Cancer or malignancy is a multifactorial disease with an approximate 9.6 million fatalities in 2018. Worldwide, it is the second leading cause of death. Bray et al. (2018). The complex modifications in the genome and epigenome affected by the interactions between host and environment lead to cancer development and progression. Despite advancements in characterizing the molecular mechanisms of oncogenesis, tumor progression and metastasis (Coyle et al. (2017)), delayed cancer detection, limited surgical options, therapeutic resistance, and tumor recurrence are serious obstacles in decreasing the prevalence and mortality rate of cancer. Since metastasis is the primary cause of deaths from cancer, early detection and the design of therapeutic approaches that target mechanisms of multi-step/multi-faceted metastasis are essential.

There is a need for improved materials and methods for early detection as well as improved therapeutic approaches that target mechanisms of metastasis.

BRIEF SUMMARY OF THE INVENTION

Several pathways have been shown to contribute to metastasis of malignant tumors. ASPH is a key player in the malignant transformation of solid tumors by enhancing cell proliferation, migration, invasion, stemness, angiogenesis, lymphogenesis, transmigration, dormancy-reactivation-overgrowth at distant sites. ASPH also promotes tumor growth by inducing immunosuppression. These effects are partially achieved via the activation of Notch, TGFβ, HGF-cMET, HIF, and SRC signaling pathways. ASPH expression is required for early embryonic development and differentiation but silenced after birth and undetectable on normal adult tissues (expect placenta) during adulthood. When ASPH is reemerged and upregulated by growth factors and hypoxia to initiate tumorigenesis and maintain malignant phenotypes in a broad-spectrum of human tumors. Compared to no or low levels, moderate to high levels of ASPH expression confer relapse/recurrence, early progression, metastasis and curtailed survival of cancer patients. Thus, targeting ASPH may have a universally profound clinical impact on cancer diagnosis, prognosis and therapy. Provided herein are new ASPH-based diagnostic and anti-metastatic strategies to improve cancer therapy outcomes.

The embodiments of this invention provide an LRC1 antibody that binds to the full-length isoform of ASPH. Although several hundred monoclonal antibodies have been produced against the ASPH protein, the LRC1 antibody of this invention provides several important advantages over these prior art. The LRC1 antibody provides improved sensitivity and specificity of assays designed for detection of early tumor formation using liquid biopsies. This is due to the unique and surprising properties of LRC1 antibody which include: (1) recognition of the full-length isoform of ASPH that has transforming activity when overexpressed in cells; (2) recognition of the full-length isoform of ASPH in tumors derived from the mesoderm such as sarcomas, leukemias and lymphomas; (3) detection of as little as 25 pg of the full-length isoform of ASPH when bound to a solid phase support; (4) detection of the full-length isoform of ASPH presence in biofluids containing ectosomes and exosomes as a companion diagnostic test of malignancy; (5) the LRC1 mAb-based immunoassay described provides a highly sensitive technique for the early cancer diagnosis by using 15-25 μL of peripheral blood derived from a finger prick involving only the use of a single LRC1 mAb and using lateral flow and micro fluidic analysis that is digitally and optically controlled and automated; (6) the exact epitope (i.e., NPVEDS (SEQ ID NO: 24)) to which LRC1 binds on the full-length isoform of ASPH, an oncofetal and oncogenic protein has been defined, which is specifically highly expressed on the surface of tumor cells and tumor cell-derived exosomes and ectosomes; and (7) the unique amino acid and nucleic acid sequences of the LRC1 mAb have been determined. The embodiments of this invention greatly advance its capability for early detection of cancer. Using a single antibody, with this degree of immunoreactivity in tumors derived from the endoderm, mesoderm and ectoderm, is unprecedented and pertains to human tumor development, progression, and metastasis.

In some embodiments, the LRC1 antibody comprises a light chain and a heavy chain, wherein the light chain comprises a light chain variable region (LCVR) and the heavy chain comprises a heavy chain variable region (HCVR). The LCVR comprises complementarity determining regions LCDR1 consisting of amino acid sequence SEQ ID NO: 5, LCDR2 consisting of amino acid sequence SEQ ID NO: 6, and LCDR3 consisting of amino acid sequence SEQ ID NO: 7. The HCVR comprises complementarity determining regions HCDR1 consisting of amino acid sequence SEQ ID NO: 2, HCDR2 consisting of amino acid sequence SEQ ID NO: 3, and HCDR3 consists of amino acid sequence SEQ ID NO: 4.

In an alternative embodiment, the LRC1 antibody that binds to the full-length isoform of ASPH comprises a light chain comprising an LCVR having the amino acid sequence SEQ ID NO: 9 and a heavy chain comprising an HCVR having the amino acid sequence SEQ ID NO: 8. In another alternative embodiment, the antibody that binds to the full-length isoform of ASPH comprises a light chain comprising the amino acid sequence SEQ ID NO: 11 and a heavy chain comprising the amino acid sequence SEQ ID NO: 10. In yet another alternative embodiment, the antibody that binds to the full-length isoform of ASPH comprises two light chains, each comprising the amino acid sequence SEQ ID NO: 11, and two heavy chains, each comprising the amino acid sequence SEQ ID NO: 10.

In another aspect, the embodiments of this invention provide a DNA molecule comprising a polynucleotide sequence encoding a light chain polypeptide having the amino acid sequence SEQ ID NO: 11. In one embodiment, the DNA molecule encoding a light chain polypeptide comprises the nucleic acid sequence SEQ ID NO: 21.

In another aspect, the embodiments of this invention provide a DNA molecule comprising a polynucleotide sequence encoding a heavy chain polypeptide having the amino acid sequence SEQ ID NO: 10. In one embodiment, the DNA molecule encoding a heavy chain polypeptide comprises the nucleic acid sequence SEQ ID NO: 20.

In another aspect, the embodiments of this invention provide a recombinant host cell comprising the DNA molecules described above. The cell can express an antibody comprising a heavy chain having the amino acid sequence SEQ ID NO: 10 and a light chain having the amino acid sequence SEQ ID NO: 11.

In another aspect, the embodiments of this invention provide a process for producing an antibody that binds to the full-length isoform of human ASPH comprising a heavy chain comprising amino acid sequence SEQ ID NO: 10 and a light chain comprising the amino acid sequence of SEQ ID NO: 11. The process includes the steps of: (i) cultivating the above-described recombinant host cell under conditions such that the ASPH mAb is expressed; and (ii) recovering the expressed antibody from the host cell.

In another aspect, the embodiments of this invention provide a pharmaceutical composition comprising an antibody described above along with one or more pharmaceutically acceptable carriers, diluents, fillers, adjuvants, conjugates, or excipients.

In another aspect, the embodiments of this invention provide a method for diagnosing a malignant neoplasm in a mammal by contacting a bodily fluid (biofluid) from the mammal with an antibody which binds to the full-length isoform of ASPH (SEQ ID NO: 1) under conditions sufficient to form an antigen-antibody complex and detecting the antigen-antibody complex. Malignant neoplasms detected in this manner include those derived from (1) endodermal tissue, e.g., head and neck cancer, thyroid cancer, thymus cancer, non-small cell lung cancer, esophageal cancer, gastric cancer, hepatocellular carcinoma, gallbladder cancer, cholangiocarcinoma, pancreatic cancer, colon and rectum cancer, renal cancer, prostate cancer, breast cancer, ovarian, fallopian tube and cervical cancer; (2) mesoderm tissue, e.g., soft tissue sarcoma, osteosarcoma, chondrosarcoma, malignant mesothelioma, myeloid leukemia, lymphoid leukemia, multiple myeloma, and lymphoma; (3) ectoderm tissue, e.g., skin cancer, melanoma, neoplasms of the central nervous system (CNS) such as primary malignant CNS neoplasms of both neuronal and glial cell origin and metastatic CNS neoplasms (e.g., glioblastoma multiforme (GBM)) are also detected. Patient derived tissue samples, e.g., biopsies of solid tumors and bodily fluids (biofluid) such as a CNS-derived cerebrospinal fluid (CSF), blood (serum), urine, saliva, sputum, lung effusion, and ascites fluid are contacted with an ASPH-specific antibody of this invention.

In another aspect, the embodiments of this invention provide a pharmaceutical composition comprising an antibody described above along with one or more pharmaceutically acceptable carriers, diluents, fillers, adjuvants, conjugates, or excipients.

The assay described herein is useful to predict prognosis of a (pre)malignant disease. A method for prognosis of a malignant neoplasm of a mammal is carried out by (a) contacting a bodily fluid from the mammal with an ASPH-specific antibody of this invention under conditions sufficient to form an antigen-antibody complex and detecting the antigen-antibody complex; (b) quantitating the amount of complex to determine the level of ASPH in the fluid; and (c) comparing the level of ASPH in the fluid with a normal tissue (with a trace or undetectable level of ASPH). An increasing level of ASPH over time indicates a progressive worsening of the disease, and therefore, an adverse prognosis. If the level of ASPH is above the reference level, the subject is identified as having a malignant neoplasm. Where the biological sample is serum, the detected level of ASPH is compared with the reference level. Where the level of ASPH is above the reference level, the subject is further provided a confirming diagnosis and subsequent treatment appropriate for the malignant neoplasm. In some embodiments, the treatment comprises administering to the subject a composition comprising a therapeutically effective amount of an ASPH-specific antibody of this invention linked to a cytotoxic agent (a substance that kills cells, including cancer cells, which may stop cancer cells from dividing and growing and may cause tumors to shrink in size), including conventional chemotherapy drugs (e.g., Doxorubicin, Paclitaxel), tubulin inhibitors (maytansinoids [DM1 and DM4] or auristatins), DNA-damaging agents (e.g., calicheamicins), Auristatins (e.g., monomethyl auristatin E (MMAE) and F (MMAF)), deruxtecan, duocarmycin, SN-38, PE38 (a 38-kDa fragment of *Pseudomonas* exotoxin A), PBD (pyrrolobenzodiazepines), radioactive isotope (e.g., alpha particles, protons), and their derivatives. The malignant neoplasms that can be diagnosed with the assay include, but are not limited to, head and neck cancer, thyroid cancer, thymus cancer, non-small cell lung cancer, esophageal cancer, gastric cancer, hepatocellular carcinoma, cholangiocarcinoma, gallbladder cancer, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, lymphoid leukemia, multiple myeloma, lymphoma, skin cancer, melanoma and glioblastoma.

The assay format described herein is also useful to generate temporal data used for prognosis of malignant disease. A method for monitoring treatment progress in a mammalian subject having of a malignant neoplasm is carried out by (a) contacting a first biological sample from the mammalian subject with an antibody which binds to the full-length isoform of ASPH under conditions sufficient to form an antigen-antibody complex and then detecting and measuring the antigen-antibody complex to determine the level of ASPH in the first sample; (b) administering to the subject a therapeutic agent for treating the malignant neoplasm; (c) contacting a second, post-treatment biological sample from the mammalian subject with an antibody which binds to the full-length isoform of ASPH under conditions sufficient to form an antigen-antibody complex and then detecting and measuring the antigen-antibody complex to determine the level of ASPH in the second sample; and (c)

comparing the levels of ASPH in the two samples. A second level measurement significantly lower than the first level measurement indicates that the therapeutic agent is effective, and vice versa. Again, the therapeutic agent can be a therapeutically effective amount of an ASPH-specific antibody of this invention linked to a cytotoxic agent. The malignant neoplasms that can be monitored with the assay include, but are not limited to, head and neck cancer, thyroid cancer, thymus cancer, non-small cell lung cancer, esophageal cancer, gastric cancer, hepatocellular carcinoma, cholangiocarcinoma, gallbladder cancer, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, lymphoid leukemia, multiple myeloma, lymphoma, skin cancer, melanoma and glioblastoma.

Diagnostic kits are also encompassed by the invention. A kit for detecting a tumor cell contains an antibody which binds to the full-length isoform of ASPH, or a functionally active fragment thereof, wherein the antibody or functionally active fragment binds to residues 286-291 of SEQ ID NO: 1. The kit optionally contains a means for detecting binding of the antibody to the tumor cell. For example, the kit contains a detectable marker, e.g., a nonradioactive marker such as $Gd^{+++}$ or $Fe^{++}$ or a radioactive compound. The kit may also contain instructions for use, a standard reagent for determining positive antibody binding, and/or a negative control for determining a lack of antibody binding. The components are packaged together in a kit. In some embodiments, the kit is a diagnostic assay formulated in a standard double-antibody sandwich binding format in which one antibody which binds to the full-length isoform of ASPH captures ASPH antigen in a patient sample and another ASPH-specific antibody is used to detect captured ASPH. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a calorimetric agent or radioisotope. The components are packaged together in a kit. The malignant neoplasms that can be diagnosed with the kit include, but are not limited to, head and neck cancer, thyroid cancer, thymus cancer, non-small cell lung cancer, esophageal cancer, gastric cancer, hepatocellular carcinoma, cholangiocarcinoma, gallbladder cancer, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, lymphoid leukemia, multiple myeloma, lymphoma, skin cancer, melanoma and glioblastoma.

Other implementations are also described and recited herein.

BRIEF DESCRIPTION OF THE DRAWINGS

For the purpose of illustration, certain embodiments of this invention are shown in the drawings described below. It should be understood, however, that the invention is not limited to the precise arrangements, dimensions, and instruments shown. In the drawings.

DETAILED DESCRIPTION OF THE INVENTION

Figure 1:
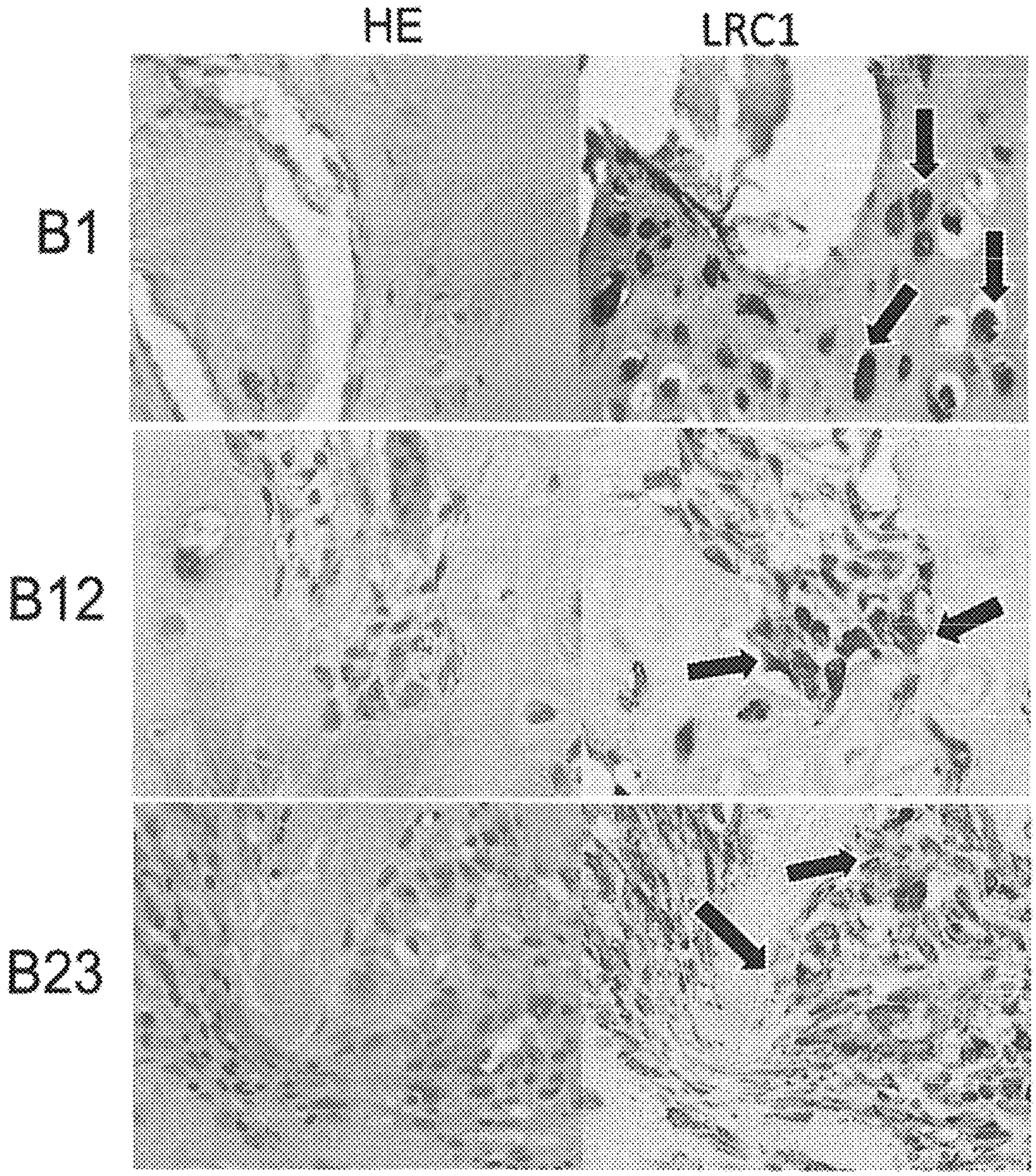
FIG. 1 shows representative examples of ASPH overexpression in human chondrosarcomas (highlighted by arrows) as shown by immunohistochemistry (IHC) using LRC1. Magnification=400×.

The innovation is now described with reference to the drawings, wherein like reference numerals are used to refer to like elements throughout. In the following description, for purposes of explanation, many specific details are set forth to provide a thorough understanding of this invention. It may be evident, however, that this invention may be practiced without these specific details. In other instances, well-known structures and devices are shown in block diagram form to facilitate describing this invention. It is to be appreciated that certain aspects, modes, embodiments, variations and features of the invention are described below in various levels of detail to provide a substantial understanding of this invention.

Definitions

For convenience, the meaning of some terms and phrases used in the specification, examples, and appended claims, are provided below. Unless stated otherwise, or implicit from context, these terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content dictates otherwise. For example, reference to "a cell" includes a combination of two or more cells.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (unless such number would be less than 0% or exceed 100% of a possible value). As used herein, reference to "approximately" or "about" a value or parameter includes and describes embodiments directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of these embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements. Using "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term allows the presence of more elements that do not materially affect the basic and novel or functional characteristic(s) of that embodiment of the invention.

The term "statistically significant" or "significantly" refers to statistical significance and generally means a two-standard-deviation (2SD) or greater difference.

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the terms "effective amount" and "therapeutically-effective amount" include an amount sufficient to prevent or ameliorate a manifestation of a disease or a medical condition, such as a malignant neoplasm. It will be appreciated that there will be many ways known in the art to determine the effective amount for a given application. For example, the pharmacological methods for dosage determination may be used in the therapeutic context. In therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of a disease. The skilled artisan can determine appropriate dosages depending on these and other factors. The compositions can also be administered combined with one or more additional therapeutic compounds.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical parameters are improved. Alternatively, treatment is "effective" if the progression of a condition is reduced or halted. "Treatment" includes not just the improvement of symptoms or parameters, but also a cessation or at least slowing down of progression or worsening of symptoms that would be expected absent treatment. Beneficial or desired clinical results include, but are not limited to, alleviation of one or more symptom(s), diminishment of extent of the deficit, stabilized (i.e., not worsening) state of a tumor or malignancy, delay or slowing down of tumor growth and/or metastasis, and an increased lifespan as compared to that expected absent treatment.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long-acting therapeutic agent or drug is used. Thus, the subject is treated for a period of at least 12 weeks. Often, long-term administration is for at least 4, 5, 6, 7, 8, 9 months or more, or for at least 1, 2, 3, 5, 7 or 10 years, or more.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intra-lymphatic, intra-lymph node, intravenous, intraportal vein, intrahepatic arterial, intramuscular, intraarterial, intrathecal, intracapsular, intra-orbital, intratumoral, intracardiac, intradermal, intraperitoneal, intranasal, intratracheal, intrathecal, transtracheal, subcutaneous, subcuticular, intraarticular, subcapsular, subarachnoid, intraspinal and intra-sternal injection and infusion. In one embodiment, the compositions contemplated herein are administered to a subject by direct injection into a tumor, lymph node, or site of infection.

The terms "decrease," "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In a marker or symptom, an "increase" is a statistically significant increase in such level.

Cancer-Related Definitions:

As used herein, the term "cancer" relates generally to a class of diseases or conditions in which abnormal cells divide out of control and can migrate and invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments, the cancer is a primary cancer. In some embodiments, the cancer is a malignant cancer also called a malignant neoplasm. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and rarely invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form solid tumors, but some, e.g., leukemias, do not necessarily form solid tumors. For those cancer cells that form solid tumors, the terms cancer (cell) and tumor (cell) are used interchangeably.

A subject that has a cancer or a tumor is a subject having objectively measurable cancer cells present in the subject's body. Included in this definition are malignant, actively proliferative cancers and potentially dormant tumors or micro-metastases. Cancers which migrate away from their original locations, invade and seed other vital organs can eventually lead to the death of the subject through the functional deterioration of the affected organs. Hemopoietic cancers, such as leukemias, can out-compete the normal hemopoietic compartments in a subject, thereby leading to hemopoietic failure, in the form of anemia, thrombocytopenia and neutropenia, ultimately causing death.

Examples of cancer include but are not limited to, carcinoma, adenocarcinoma, intra-epithelial neoplasm; blastoma such as neuroblastoma; brain and CNS cancer such as glioblastoma multiforme (GBM); cancer of the head and neck; eye cancer such as retinoblastoma; oral cavity cancer (e.g., lip, tongue, mouth, larynx and pharynx); salivary gland carcinoma; thyroid cancer; thymic carcinoma, cancer of the respiratory system such as lung cancer (e.g., small-cell lung cancer, non-small cell lung cancer, adenocarcinoma of the lung, and squamous carcinoma of the lung); cancer of the peritoneum; cancer of the digestive system; esophageal cancer; gastric/stomach cancer (including gastrointestinal cancer); hepatocellular carcinoma; hepatoma; biliary tract cancer; pancreatic cancer; colon and rectum cancer; cancer of the urinary system such as bladder cancer and kidney/renal cancer; prostate cancer; testicular cancer; breast cancer; ovarian cancer; cervical cancer; uterine or endometrial cancer; vulval cancer; skin cancer; basal cell carcinoma, squamous cell cancer; melanoma; sarcoma such as rhabdomyosarcoma, osteosarcoma and chondrosarcoma; connective tissue cancer; leukemia, bone cancer; lymphoma including Hodgkin's and non-Hodgkin's lymphoma; multiple myeloma; other carcinomas and sarcomas; and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD) and abnormal vascular proliferation associated with phakomatoses, edema (such as that associated with brain tumors), and Meigs' syndrome.

A "cancer cell" is a cancerous, pre-cancerous, malignancy, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, loss of contact inhibition or density limitation of growth, growth factor or serum independence, upregulated/highly expressed tumor specific markers, invasiveness or metastasis, and tumor growth in suitable animal hosts such as immunocompromised, immunodeficient or even immunocompetent (for mouse derived cancer) mice.

A subject can be one who has been diagnosed with or identified as suffering from or having a condition in need of treatment (e.g., a cancer) or one or more complications related to such a condition, and optionally, but need not have already undergone treatment for a condition or the one or more complications related to the condition. A subject can also be one who has not been previously diagnosed as having a condition in need of treatment or one or more complications related to such a condition. For example, a subject can exhibit one or more risk factors for a condition, or one or more complications related to a condition or a subject who does not exhibit risk factors. A "subject in need" of treatment for a particular condition can be a subject having that condition, diagnosed as having that condition, or at risk of developing that condition.

Biopharmaceutical Definitions:

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, sumoylated, farnesylated, etc.) and amino acid analogs, regardless of its size or function. "Protein" and "polypeptide" are often used in reference to relatively large polypeptides, but the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skills will recognize that individual substitutions, deletions, insertions or suppressor mutations to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions, substitutions or suppressor mutations. Variant polypeptide-encoding DNA sequences encompass sequences that comprise one or more insertions, deletions, or substitutions of nucleotides when compared to a native or reference DNA sequence, but that encode a variant protein or fragment thereof that retains activity or function. A wide variety of PCR-based site-directed mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid, or artificial nucleic acid analogues (e.g., peptide nucleic acid, morpholino- and locked nucleic acid, glycol nucleic acid, threose nucleic acid and hexitol nucleic acid), or any analogs thereof. The nucleic acid can be single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell is typically still referred to as "engineered" even though the actual manipulation was performed on a prior entity.

In some embodiments, a nucleic acid encoding a polypeptide as described herein (e.g., an antibody or antibody reagent) is comprised by a vector. In some respects, described herein, a nucleic acid sequence encoding a given polypeptide as described herein, or any module thereof, is operably linked to a vector. A vector can include, but is not limited to, a cloning vector, an expression vector, a plasmid, phage, transposon, cosmid, chromosome, virus, oncolytic virus-like vesicle (VLV), virion, extracellular vesicles, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise more elements, for example, the expression vector may have two replication systems, thus allowing it to be maintained in two organisms, for example in human cells for expression and in a prokaryotic host for cloning and amplification. The term "expression" refers to the cellular processes involved in producing RNA, peptides and proteins, and as appropriate, secreting peptides or proteins, including where applicable, but not limited to transcription, transcript processing, translation and protein folding, modification, degradation, shuttling, shuffling, and processing. "Expression products" include RNA transcribed from a gene, and polypeptides obtained by translation of mRNA transcribed from a gene. The term "gene" means the nucleic acid sequence which is transcribed (DNA) to RNA in vitro, ex vivo or in vivo when operably linked to appropriate regulatory sequences. The gene might include regions preceding and following the coding region, e.g., 5' untranslated (5'UTR) or "leader" sequences and 3' UTR, "trailer" or "leader" sequences, as well as intervening sequences (introns) or spacers between individual coding segments (exons).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including at least 96%, at least 97%, at least 98%, at least 99% or more. In some embodiments, the antibody, antigen-binding portion (e.g., scFv or nanobody) thereof, bispecific or tri-specific T cell engager, bispecific or tri-specific NK cell engager, immune cell recruiter, or chimeric antigen receptor (CAR) described herein is isolated. In some embodiments, the antibody, antibody reagent, antigen-binding portion thereof, engager, recruiter or CAR described herein is purified.

As used herein, "engineered" refers to the aspect of having been manipulated by the hand of man. For example, an antibody, antibody reagent, antigen-binding portion (e.g., scFv or nanobody) thereof, or tri-specific T cell engager, bispecific or tri-specific NK cell engager, immune cell recruiter (such as Bifunctional checkpoint-inhibitory T cell engager (CiTE), simultaneous multiple interaction T cell engager (SMITE), immune-mobilizing monoclonal TCRs against cancer (ImmTACs)), CAR or is considered "engineered" when the sequence of the antibody, antibody reagent, antigen-binding portion thereof, engager, recruiter or CAR is manipulated by the hand of man to differ from the sequence of an antibody as it exists in nature. As is common practice and is understood by those in the art, progeny and copies of an engineered polynucleotide and/or polypeptide are typically still called "engineered" even though the actual manipulation was performed on a prior entity.

Antibody-Related Definitions:

As used herein, an "epitope" can be formed on a polypeptide both from contiguous amino acids, and noncontiguous amino acids juxtaposed by tertiary folding of a protein. Epitopes formed from contiguous amino acids are typically retained on exposure to denaturing solvents, but epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody and represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains and a variety of forms including full length antibodies and antigen-binding portions thereof; including an immunoglobulin molecule, a monoclonal antibody, a chimeric antibody, a CDR-grafted antibody, a humanized antibody, a Fab, a Fab', a $F(ab')_2$, a Fv, a disulfide linked Fv, a scFv, a single domain antibody (dAb), a diabody, a nanobody, a multi-specific (e.g., tri-specific) antibody, a dual specific antibody, a bispecific antibody, an anti-idiotypic antibody, a functionally active epitope-binding portion thereof, and/or bifunctional hybrid antibodies.

Each heavy chain comprises a variable region of the heavy chain (abbreviated here as HCVR or VH) and a constant region of the heavy chain (CH). The heavy chain constant region consists of three domains CH1, CH2 and CH3. Each light chain comprises a variable region of the light chain (abbreviated here as LCVR or VL) and a constant region of the light chain (CL). The light chain constant region consists of a CL domain. The VH and VL regions may be further divided into hypervariable regions called complementarity-determining regions (CDRs) and interspersed with conserved regions called framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat et al. (1987 and 1991) not only provides an unambiguous residue numbering system applicable to any variable region of an antibody, but also provides precise residue boundaries defining the three CDRs. These CDRs may be called Kabat CDRs. Other boundaries defining CDRs overlapping with the Kabat CDRs have been described by Padlan (1995), MacCallum (1996), Chothia & Lesk (1987), and Chothia et al. (1989). Still other CDR boundary definitions may not strictly follow one of the above systems, but will still overlap with the Kabat CDRs, although they may be shortened or lengthened, given prediction or experimental findings those residues or groups of residues or even entire CDRs do not significantly affect antigen binding. The methods used herein may use CDRs defined according to any of these systems, although preferred embodiments use Kabat defined CDRs.

The term "antigen-binding portion" of an antibody refers to one or more portions of an antibody as described herein, said portions still having the binding affinities and avidities as defined above herein. Portions of a complete antibody have been able to carry out the antigen-binding function of an antibody. Under the term "antigen-binding portion" of an antibody, examples of binding portions include (i) an Fab portion, i.e., a monovalent portion composed of the VL, VH, CL and CH1 domains; (ii) an $F(ab')_2$ portion, i.e., a bivalent portion comprising two Fab portions linked to one another in the hinge region via a disulfide bridge; (iii) an Fd portion composed of the VH and CH1 domains; (iv) an Fv portion composed of the VL and VH domains of a single arm of an antibody; and (v) a dAb portion consisting of a VH domain or of VH, CH1, CH2, DH3, or VH, CH2, CH3 (dAbs, or single domain antibodies, comprising only VL domains have also been shown to specifically bind to target epitopes). Although the two domains of the Fv portion, namely VL and VH, are encoded by separate genes, they may further be linked to one another using a synthetic linker, e.g., a poly-G4S (SEQ ID NO: 22) amino acid sequence ('G4S (SEQ ID NO: 22)' disclosed as SEQ ID NO: 29 in U.S. Pat. No. 10,253,111), and recombinant methods, making it possible to prepare them as a single protein chain in which the VL and VH regions combine to form monovalent molecules (known as single chain variable fragment (scFv)). The term "antigen-binding portion" of an antibody is also intended to comprise such single chain antibodies. Other forms of single chain antibodies such as nanobody, "diabodies" are likewise included here. Truncated versions (modified single-variable domains) of heavy-chain antibodies (HCAbs, VHH) from camelids, also termed nanobodies, comprise only one-tenth the mass of conventional antibodies, yet retain similar, high binding affinities for the antigens. Diabodies are bivalent, bispecific antibodies in which VH and VL domains are expressed on a single polypeptide chain but using a linker too short for the two domains combining on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments and complete antibodies.

An antibody can have the structural features of IgA, IgG, IgE, IgD, IgM (and subtypes and combinations thereof). Antibodies can be from any source, including mouse, rabbit, pig, rat, and primate (human and non-human primate) and primatized (e.g., macaque/human chimeric) antibodies. Antibodies also include microbodies (an artificial short chain of amino acids copied from a fully functional natural antibody), midibodies, humanized antibodies, chimeric (e.g., mouse/human) antibodies.

An antibody, antigen-binding portion thereof, engager, recruiter or CAR as described herein may be part of a larger immunoadhesion molecule formed by covalent or noncovalent association of the antibody or antibody portion with one or more further proteins or peptides. Relevant to such immunoadhesion molecules are the use of the streptavidin core region to prepare a tetrameric scFv molecule and the use of a cysteine residue, a marker peptide and a C-terminal polyhistidinyl, e.g., hexahistidinyl tag (SEQ ID NO: 23) ('hexahistidinyl tag (SEQ ID NO: 23)' disclosed as SEQ ID NO: 30 in U.S. Pat. No. 10,253,111) to produce bivalent and biotinylated scFv molecules.

In some embodiments, the antibody, antibody reagent, antigen-binding portion thereof, engager, recruiter or CAR described herein can be an immunoglobulin molecule, a monoclonal antibody, a chimeric antibody, a CDR-grafted antibody, a primatized antibody, a humanized antibody, a fragment antibody, a Fab, a Fab', a F(ab')2, a Fv, a disulfide linked Fv, a scFv, a single domain antibody, a multi-domain antibody, a multi-specific (e.g., tri-specific) antibody, a dual specific antibody, a bispecific antibody, an anti-idiotypic antibody, a diabody, a nanobody, a microbody, a midibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody, primatized antibody or antibody reagent. In some embodiments, the antibody, antigen-binding portion thereof, is a recombinant polypeptide. In some embodiments, the CAR comprises an extracellular domain that binds the full-length isoform of ASPH, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (1991). However, the human antibodies can contain amino acid residues not encoded by human germ line immunoglobulin sequences (for example mutations introduced by random or site-directed mutagenesis in vitro or by somatic mutation in vivo), for example in the CDRs, and in particular in CDR3. Recombinant human antibodies as described herein have variable regions and may also contain constant regions derived from immunoglobulin sequences of the human germ line. See Kabat et al. (1991). According to particular embodiments, however, such recombinant human antibodies are subjected to in vitro mutagenesis (or to a somatic in vivo mutagenesis, if an animal is used which is transgenic due to human Ig sequences) so the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies result from selective mutagenesis or back mutation (a change in a nucleotide pair in a mutant gene that restores the original sequence and hence the original phenotype, a process causing reversion) or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps used to humanize a monoclonal antibody, see, e.g., U.S. Pat. Nos. 5,585,089; 6,835,823; and 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

In some embodiments, the antibody, antibody reagent, antigen-binding portion thereof, engager, recruiter, and/or CAR as described herein can be a variant of a sequence described herein, e.g., a conservative substitution variant of an antibody polypeptide. In some embodiments, the variant is a conservatively changed variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions, substitutions, or suppressor mutations. Variant polypeptide-encoding DNA sequences encompass sequences that comprise one or more additions, deletions, substitutions or suppressor mutations of nucleotides when compared to a native or reference DNA sequence, but that encode a variant protein or portion thereof that retains activity, e.g., antigen-specific binding activity for the relevant target polypeptide, e.g., the full-length isoform of ASPH. A wide variety of PCR-based site-specific mutagenesis approaches are also known in the art and can be applied by the ordinarily skilled artisan.

Usually, the CDR regions in humanized antibodies and human antibody variants are substantially identical, and more usually, the same as the corresponding CDR regions in the mouse or human antibody from which they were derived. In some embodiments, it is possible to make one or more conservative amino acid substitutions of CDR residues without noticeably affecting the binding affinity or avidity of the resulting humanized immunoglobulin or human antibody variant. In some embodiments, substitutions of CDR regions can enhance binding affinity and/or avidity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (called the donor immunoglobulin). The constant region(s), if present, are also substantially or entirely from a human immunoglobulin. The human variable domains are usually chosen from human antibodies whose framework sequences show a high degree of sequence identity with the (e.g., murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species (e.g., rat, rabbit), antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated using well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, a recombinant humanized antibody can be further optimized to decrease potential immunogenicity, while maintaining functional activity, for therapy in humans. Functional activity means a polypeptide capable of displaying one or more known functional activities associated with a recombinant antibody, antigen-binding portion thereof, or CAR as described herein. Such functional anti-cancer activities include recognizing, binding to, and directly or indirectly killing cancer cells. Additionally, a polypeptide having functional activity means the polypeptide shows activity similar, but not necessarily the same as, an activity of a reference antibody, antigen-binding portion thereof, engager, recruiter or CAR as described herein, including mature forms, as measured in a particular assay, such as, for example, a biological assay, with or without dose dependency. Where dose dependency exists, it need not be identical to that of the reference antibody, antigen-binding portion thereof, engager, recruiter or CAR, but rather substantially similar to the dose-dependence in a given activity as compared to the reference antibody, antigen-binding portion thereof, engager, recruiter or CAR as described herein (i.e., the candidate polypeptide will show greater activity, or not more than about 25-fold less, about 10-fold less, or about 3-fold less activity relative to the antibodies, antigen-binding portions, engager, recruiter and/or CARs described herein).

In some embodiments, the antibody reagents (e.g., antibodies, engager, recruiter or CARs) described herein are not naturally occurring biomolecules. For example, a murine antibody raised against an antigen of human origin would not occur in nature without human intervention and manipulation, e.g., manufacturing steps carried out by a human. Chimeric antibodies are also not naturally occurring biomolecules, e.g., because they comprise sequences obtained from multiple species and assembled into a recombinant molecule. In certain particular embodiments, the human antibody reagents described herein are not naturally occurring biomolecules, e.g., fully human antibodies directed against a human antigen would be subject to negative selection in nature and are not naturally found in the human body.

In some embodiments, the antibody, antibody reagent, antigen-binding portion thereof, engager, recruiter and/or CAR is an isolated polypeptide. In some embodiments, the antibody, antibody reagent, antigen-binding portion thereof, engager, recruiter and/or CAR is a purified polypeptide. In some embodiments, the antibody, antibody reagent, antigen-binding portion thereof, engager, recruiter and/or CAR is an engineered polypeptide.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant ($K_D$ of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant ($K_A$) of $10^5$ to $10^{12}$ liter/moles or more, such as $10^7$ to $10^{12}$ liter/moles or $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction, the lower is its $K_D$. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as a radioimmunoassay (RIA), sandwich competition assay, enzyme-linked immunosorbent assay (ELISA), antigen down assay, enzyme immunoassay (EIA), and the different variants thereof known per se in the art; as well as other techniques as mentioned herein.

As used herein, "selectively binds" or "specifically binds" refers to the ability of a peptide (e.g., an antibody, engager, recruiter, CAR, or portion thereof) described herein to bind to a target, such as an antigen present on the cell-surface of a cancer cell, with a $K_D$ $10^{-5}$ M (10000 nM) or less, e.g., $10^{-6}$ M, $10^{-7}$M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to an antigen on a target is not displaced by a non-similar competitor. In certain embodiments, an antibody, antigen-binding portion thereof, engager, recruiter, or CAR is said to specifically bind an antigen when it preferentially recognizes its target antigen in a complex mixture of proteins and/or macromolecules.

In some embodiments, an antibody, antigen-binding portion thereof, engager, recruiter, or CAR, as described herein, binds to the full-length isoform of ASPH with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody, antigen-binding portion thereof, engager, recruiter, or CAR, as described herein, binds to the full-length isoform of ASPH with a dissociation constant ($K_D$) of from about $10^{-5}$ M to $10^{-6}$ M. In some embodiments, an antibody, antigen-binding portion thereof, engager, recruiter, or CAR, as described herein, binds to the full-length isoform of ASPH with a dissociation constant ($K_D$) of from about $10^{-6}$ M to $10^{-7}$ M. In some embodiments, an antibody, antigen-binding portion thereof, engager, recruiter, or CAR, as described herein, binds to the full-length isoform of ASPH with a dissociation constant ($K_D$) of from about $10^{-7}$ M to $10^{-8}$ M. In some embodiments, an antibody, antigen-binding portion thereof, engager, recruiter, or CAR, as described herein, binds to the full-length isoform of ASPH with a dissociation constant ($K_D$) of from about $10^{-8}$ M to $10^{-9}$ M. In some embodiments, an antibody, antigen-binding portion thereof, engager, recruiter, or CAR, as described herein, binds to the full-length isoform of ASPH with a dissociation constant ($K_D$) of from about $10^{-9}$ M to $10^{-10}$ M. In some embodiments, an antibody, antigen-binding portion thereof, engager, recruiter, or CAR, as described herein, binds to the full-length isoform of ASPH with a dissociation constant ($K_D$) of from about $10^{-10}$ M to $10^{-11}$ M. In some embodiments, an antibody, antigen-binding portion thereof, engager, recruiter, or CAR, as described herein, binds to the full-length isoform of ASPH with a dissociation constant ($K_D$) of from about $10^{-11}$ M to $10^{-12}$ M. In some embodiments, an antibody, antigen-binding portion thereof, engager, recruiter, or CAR, as described herein, binds to the full-length isoform of ASPH with a dissociation constant ($K_D$) of less than $10^{-12}$ M.

Pharmaceutical Compositions

The compositions and methods of this invention may be used to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive, corn, sunflower, grapeseed, vegetable, fish oil, or injectable organic esters. In preferred embodiments, when such pharmaceutical compositions are for human administration, particularly for invasive routes of administration (i.e., routes, such as injection, pump infusion, transplantation or implantation, that circumvent transport or diffusion through an epithelial barrier), the aqueous solution is pyrogen-free, or substantially pyrogen-free. The excipients can be chosen, for example, to effectuate delayed release of an agent or to selectively target one or more cells, tissues or organs. The pharmaceutical composition can be in dosage unit form such as tablet, pill, capsule (including sprinkle capsule and gelatin capsule), granule, lyophile for reconstitution, powder, solution, syrup, suppository, gel, spray, aerosol (e.g., pressurized intraperitoneal aerosol), radioactive isotope, intervention (e.g., transarterial embolization, radiofrequency ablation), injection, infusion or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, decrease degradation, rejection or clearance, increase solubility, increase immunogenicity, or to increase the absorption of a compound such as a compound of the invention. Such physiologically acceptable agents include, for example, carbohydrates, such as glucose, sucrose or dextrans; antioxidants, such as ascorbic acid or glutathione; chelating agents; low molecular weight proteins; adjuvants (e.g., Alum, MF59, AS01/03/04, CpG1018) or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, metals, radioactive isotope/radiation particles, and/or dosage forms which are, within the scope of sound medical judgment, suitable for use in contact with the tissues of human beings and animals without excessive toxicity, irritation, allergic response, rejection, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, vegetable oil, cottonseed oil, safflower oil, sesame oil, olive oil, sunflower oil, grapeseed oil, fish oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, matrigel or hydrogel; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) nanoparticles such as liposomes, polymers, micelles, metal nanoparticles, carbon nanotubes, solid lipid nanoparticles, noisomes, and dendrimers; (22) extracellular vesicles; and (23) other non-toxic compatible substances used in pharmaceutical formulations.

A pharmaceutical composition (preparation) can be administered to a subject by any of several routes of administration including orally (for example, drenches as in aqueous or non-aqueous solutions or suspensions, tablets, pills, suppository, patch, paste, infusion pumps, capsules (including sprinkle capsules and gelatin capsules), boluses, powders, granules, pastes for application to the tongue); absorption through the oral, nasal, urinary, rectal or vaginal mucosa (e.g., sublingually, aerosol); subcutaneously; intradermally, transdermally (for example as a patch applied to the skin); intramuscularly; intravenously; and topically (for example, as a cream, lotion, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4, 172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending on the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of this invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes each containing a predetermined amount of a compound of this invention as an active ingredient. Compositions or compounds may also be administered as a bolus, electuary or paste.

To prepare solid dosage forms for oral administration, capsules, including sprinkle capsules and gelatin capsules, (coated and uncoated, bi-layer, mini-) tablets, pills, dragées, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, gel, hydrogel, matrigel, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as modified and unmodified cyclodextrins; (11) flavoring agents; (12) thermoregulation (cooling or heating) agents; and (13) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars and high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragées, capsules (including sprinkle capsules and gelatin capsules), pills and granules, may optionally be scored or prepared with coatings and shells, such as enteric coatings and other coatings well known in the pharmaceutical-formulating art. They may also be formulated to provide slow or controlled release of the active ingredient therein using, for example, hydroxypropyl methyl cellulose in varying proportions to provide the desired release profile, other polymer matrices, nanoparticles such as liposomes, and/or microspheres. They may be sterilized by, for example, filtration through a bacteria-retaining filter, or by incorporating sterilizing agents as sterile solid compositions that can be dissolved in sterile water, or some other sterile injectable medium right before use. These compositions may also optionally contain opacifying agents and may be of a composition that they release the active ingredient(s) only, or preferentially, in a certain portion of the respiratory, urogenital, gastrointestinal tract, optionally, in a delayed manner. Examples of embedding compositions that can be used include polymeric substances and waxes. The active ingredient can also be in microencapsulated form, extracellular vesicle form, if appropriate, with one or more of the above-described excipients.

Liquid dosage forms useful for oral administration include pharmaceutically acceptable emulsions, lyophiles for reconstitution, micro-emulsions, microcapsules, solutions, suspensions, syrups and elixirs. In addition to the active ingredient, the liquid dosage forms may have inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., fish, cottonseed, groundnut, corn, germ, vegetable, grapeseed, sunflower, olive, castor and sesame), glycerol, tetrahydrofurfuryl alcohol, polyethylene glycols and fatty acid esters of sorbitan, and mixtures thereof.

Besides inert diluents, the oral compositions can also include adjuvants such as Alum, MF59, AS01/03/04, CpG1018, wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, creams, lotions, ointments, gels, hydrogel, matrigel, solutions, patches, pastes, microneedles (for transdermal, intraocular, vaginal, transungual, cardiac, vascular, gastrointestinal and intracochlear delivery) and inhalants. The active compound may be mixed under sterile conditions with a pharmaceutically acceptable carrier, adjuvant, and with any preservatives, buffers, or propellants that may be required.

The ointments, creams, lotions, patches, pastes, and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches, pastes and microneedles have the added advantage of providing controlled delivery of a compound of this invention to the body. Such dosage forms can be made by dissolving or dispersing the active compound in the proper medium. Absorption enhancers can also be used to increase the flux of the compound across the skin. The rate of this flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intra-articular, intra-lymph node, intra-lymphatic, intratumoral, intrathecal, intracapsular, intraorbital, intracardiac, intradermal, intracochlear, intraperitoneal, intravaginal, transdermal, transtracheal, transungual, subcutaneous, subcuticular, intraarticular, subcapsular, subarachnoid, intraspinal, and intrasternal injection and infusion. Pharmaceutical compositions suitable for parenteral administration comprise one or more active compounds combined with one or more pharmaceutically acceptable sterile isotonic aqueous or nonaqueous solutions, dispersions, suspensions or emulsions, or sterile powders which may be reconstituted into sterile injectable solutions or dispersions just before use, which may contain antioxidants, buffers, bacteriostats, solutes which render the formulation isotonic with the blood of the intended recipient or suspending or thickening agents.

Examples of suitable aqueous and nonaqueous carriers that may be used in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be used in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity (flow/adhesion ratio) can be maintained, for example, by using coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial, antiviral and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by including agents that delay absorption such as aluminum monostearate and gelatin.

Sometimes, to prolong the effect of a drug, it is desirable to slow the absorption of the drug from subcutaneous or intramuscular injection. This may be done by the use of a liquid suspension of crystalline or amorphous material having poor water solubility. The rate of absorption of the drug then depends on its rate of dissolution. The rate of dissolution may depend on crystal size and crystalline form. Delayed absorption of a parenterally administered drug form is done by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in nanoparticles such as liposomes, extracellular vesicles, microencapsulations or microemulsions that are compatible with body tissue.

For use in the methods of this invention, active compounds can be given per se or as a pharmaceutical composition containing, for example, 0.1 to 99.5% (more preferably, 0.5 to 90%) of active ingredient combined with a pharmaceutically acceptable carrier.

Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels, matrigel), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level depends on a variety of factors including the activity of the particular compound or combination of compounds employed, or the ester, salt or amide thereof, the route of administration, the time of administration, the rate of excretion or clearance of the particular compound(s) being employed, the duration or frequency of the treatment, other drugs that may interact with or affect the metabolism or efficacy of the compound of the invention, compounds and/or materials (e.g., vaccines, antibodies and derivatives) used combined with the particular compound(s) employed, other therapeutic approaches (e.g., surgery, cell-based therapy, chemotherapy, radiotherapy, interventional therapy), the age, sex, body weight, conditions or comorbidities, diet, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required to achieve the desired therapeutic effect and gradually increase the dosage until the desired effect is achieved. By "therapeutically effective amount" is meant the concentration of a compound sufficient to elicit the desired therapeutic effect. The effective amount of the compound varies according to the body weight, sex, age, comorbidities, and medical history of the subject. Other factors which influence the effective amount may include, but are not limited to, the severity of the patient's condition, the disorder being treated, therapeutic approaches, the stability of the compound, and, if desired, another type of therapeutic agent being administered with the compound of the invention. A larger total dose can be delivered by multiple administrations of the agent. Methods to determine efficacy and dosage are known to those skilled in the art. See, e.g., Isselbacher et al. (1996).

A suitable daily dose of an active compound used in the compositions and methods of the invention could be that amount of the compound that is the lowest dose effective to produce a therapeutic effect. Such an effective dose generally depends on the factors described above.

If desired, the effective daily dose of the active compound may be administered as one, two, three, four, five, six or more sub-doses administered separately at appropriate intervals throughout the day, optionally, in unit dosage forms. In certain embodiments of this invention, the active compound are administered two or three times daily. In other embodiments, the active compound is administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone, conjointly administered with another type of therapeutic agent, or combined with a therapeutic approach, e.g., surgery, chemotherapy, radiotherapy, and interventional therapy.

This disclosure includes the use of pharmaceutically acceptable salts of compounds of the invention in the compositions and methods of this invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, lithium, L-lysine, magnesium, 4-(2-hydroxyethyl) morpholine, piperazine, potassium, 1-(2-hydroxyethyl) pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, l-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, l-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of this solvate can be from the solvent of crystallization, inherent in the solvent of preparation or crystallization, or adventitious to such solvent.

Wetting agents, emulsifiers, dispersants and lubricants, such as sodium lauryl sulfate and magnesium stearate, as well as coloring agents, release agents, coating agents, sweetening, cooling or heating agents, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, polyunsaturated fatty acids (PUFAs) such as Omega-3 fatty acids, and the like; and (3) metal-chelating agents, such as citric acid, ethylenediamine tetraacetic acid (EDTA), sorbitol, tartaric acid, phosphoric acid, succimer (dimercaptonol), dimercaprol (BAL), and the like.

Unless otherwise defined herein, scientific and technical terms used in connection with this application shall have the meanings commonly understood by those of ordinary skill in the art to which this disclosure belongs. It should be understood that this invention is not limited to the particular methodology, protocols, animal models, (engineered or genetically modified) cells, organoids, constructs, vectors, carriers, adjuvants, compounds, drug delivery system, antibodies and derivatives, vaccines, and reagents, etc., described herein and as such can vary. The terminology used herein is for the purpose of describing particular embodiments only and is not intended to limit the scope of this invention, which is defined solely by the claims. Definitions of common terms in immunology and molecular biology can be found in The Merck Manual of Diagnosis and Therapy; The Encyclopedia of Molecular Cell Biology and Molecular Medicine; Molecular Biology and Biotechnology: a Comprehensive Desk Reference; Immunology; Janeway's Immunobiology; Lewin's Genes XI; Molecular Cloning: A Laboratory Manual.; Basic Methods in Molecular Biology; Laboratory Methods in Enzymology; Current Protocols in Molecular Biology (CPMB); Current Protocols in Protein Science (CPPS); and Current Protocols in Immunology (CPI).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering with no substantial medical benefit to man or animal and animals resulting from such processes.

Other terms are defined herein within the description of the aspects of the invention.

Aspartate Beta-Hydroxylase (ASPH)

Many pathways have been shown to contribute to multi-step and multi-faceted metastasis of malignant tumors. Aspartate β-hydroxylase (ASPH) is a key player in the aggressive transformation of malignancies by enhancing cell proliferation, migration, invasion, transmigration, angiogenesis, lymphogenesis, and dormancy-reactivation-outgrowth at distant sites. ASPH also promotes tumor growth by induction of immunosuppression. These prooncogenic pathological properties are partially achieved via the activation of Notch, TGFβ, HGF-cMET, HIF and SRC signaling pathways. ASPH expression is transcriptionally upregulated by growth factors and hypoxia in different human tumors and specifically targeting this biomarker may have a broad clinical impact on diagnosis, prognosis and therapy.

ASPH is a naturally occurring enzyme that was initially identified by expression cloning of a cDNA library from a cancerous hepatobiliary cell line. Korioth et al. (1994); Lavaissiere et al. (1996). There are twelve known splice isoforms of ASPH. It has been settled that isoform 1 is expressed developmentally, minimally expressed in normal tissues, and then re-expressed at high levels in multiple malignancies (such as carcinomas). Jia et al. (1992); Patel et al. (2014). Some isoforms lack the C-terminus, that contains the catalytic site for the transforming enzymatic activity. ASPH truncated homologs Junctin and Humbug are expressed in multiple normal tissues relate principally to calcium homeostasis. Isoform 1 is the only one overexpressed in tumors derived from the endoderm, mesoderm and ectoderm.

TABLE 1 shows the amino acid sequence of ASPH (SEQ ID NO: 1; GENBANK Accession No. S83325; His motif is underlined; conserved sequences within the catalytic domain are designated by bold type).

TABLE 1

| ASPH amino acid sequence | | | | | | |
|---|---|---|---|---|---|---|
| MAQRKNAKSS | GNSSSSGSGS | GSTSAGSSSP | GARRETKHGG | HKNGRKGGLS | GTSFFTWFMV | 61 |
| IALLGVWTSV | AVVWFDLVDY | EEVLGKLGIY | DADGDGDFDV | DDAKVLLGLK | ERSTSEPAVP | 121 |
| PEEAEPHTEP | EEQVPVEAEP | QNIEDEAKEQ | IQSLLHEMVH | AEHVEGEDLQ | QEDGPTGEPQ | 181 |
| QEDDEFLMAT | DVDDRFETLE | PEVSHEETEH | SYHVEETVSQ | DCNQDMEEMM | SEQENPDSSE | 241 |
| PVVEDERLHH | DTDDVTYQVY | EEQAVYEPLE | NEGIEITEVT | APPEDNPVED | SQVIVEEVSI | 301 |
| FPVEEQQEVP | PETNRKTDDP | EQKAKVKKKK | PKLINKFDKT | IKAELDAAEK | LRKRGKIEEA | 361 |
| VNAFKELVRK | YPQSPRARYG | KAQCEDDLAE | KRRSNEVLRG | AIETYQEVAS | LPDVPADLLK | 421 |
| LSLKRRSDRQ | QFLGHMRGSL | LTLQRLVQLF | PNDTSLKNDL | GVGYLLIGDN | DNAKKVYEEV | 481 |
| LSVTPNDGFA | KVHYGFILKA | QNKIAESIPY | LKEGIESGDP | GTDDGRFYFH | LGDAMQRVGN | 541 |
| KEAYKWYELG | HKRGHFASVW | QRSLYNVNGL | KAQPWWTPKE | TGYTELVKSL | ERNWKLIRDE | 601 |
| GLAVMDKAKG | LFLPEDENLR | EKGDWSQFTL | WQQGRRNENA | CKGAPKTCTL | LEKFPETTGC | 661 |
| **RRG**QIKYSI**M** | **HP**GTHVWPHT | GPTNCRLRMH | LGLVIPKEGC | KIRCANETRT | WEEGKVLIFD | 721 |
| DSFEHEVWQD | ASSFRLIFIV | DVWHPELTPQ | QRRSLPAI SEQ ID NO: 1 | | | |

The ASPH antibodies of this invention (described below) bind to a polypeptide within the full length ASPH isoform amino acid sequence determine to be NPVEDS (SEQ ID NO: 24, residues 286-291 of SEQ ID NO: 1, shown as shadowed residues in TABLE 1). NPVEDS (SEQ ID NO: 24) is the LRC1 epitope because the binding of LRC1 to the full-length isoform of ASPH protein was abolished by peptide inhibition using this sequence and no other sequence that binds to other regions of the molecule (data not shown).

Functionally, overexpression of ASPH causes tumor cell proliferation, migration, invasion, transmigration, angiogenesis, lymphogenesis, stemness, colonization and dormancy-reactivation-outgrowth at distant sites by: (1) promoting activation of the Notch, TGFβ, HGF-cMET, HIF and SRC signaling cascades; (2) inhibiting apoptosis through caspase 3 cleavage; (3) enhancing cell proliferation via phosphorylation of RB1; (4) regulating cell senescence; (5) generating cancer stem-cell like progenitors; and (6) disrupting immune system and inducing immunosuppression. Dong et al. (2015); Huang et al. (2016); & Iwagami et al. (2016). The transcriptional regulation of ASPH expression in human tumors is controlled by well-known growth factor and cytokine signaling cascades, such as insulin/IRS-1/RAF/RAS/MAPK/ERK, insulin/IRS-1/PI3K/AKT, and WNT/β-catenin signaling. Iwagami et al. (2016).

In this context, ASPH is a key molecule linking upstream growth factors, chemokines and cytokines to prooncogenic signaling pathways, such as Notch activation and subsequent downstream expression of Notch target genes. Notch signaling is a well-recognized pathologic feature of cancer. Notch signaling promotes tumor growth and metastasis by transcriptionally upregulating the expression of cytokines and proteinases, such as matrix metalloproteinases (MMPs) and growth factors (such as VEGF). Engin et al. (2009); Xu et al. (2016). Tissue invasion by tumor cells and tumor-induced angiogenesis both require the participation of MMPs. Fang et al. (2000). MMPs expression may be an independent marker of poor prognosis. Berend et al. (1998). In this context, Isoform 1 is the only isoform with aspartyl/asparaginyl β-hydroxylase activity, which is necessary for Notch activation.

ASPH is a member of the α-ketoglutarate-dependent dioxygenase family. Hou et al. (2011); Jawad et al. (2010). ASPH catalyzes the hydroxylation of aspartyl and asparaginyl residues in epidermal growth factor (EGF) like repeats of various proteins required for signal transduction, including Notch receptors and ligands. ASPH is conserved in mammalian evolution and the human protein sequence is 85% identical to rats and mice; the catalytic site in the C-terminal region is 100% conserved among the three species. As an oncofetal protein expressed during embryonic development and differentiation, ASPH is “shut off” at birth and during adulthood, only to re-emerge during oncogenesis. Re-expression/re-activation of ASPH stimulates cell proliferation, migration, invasion, transmigration, angiogenesis, lymphogenesis, stemness, colonization and dormancy-reactivation-outgrowth at distant sites and is proposed to generate and maintain malignant phenotypes in cancer. Dong et al. (2015); Huang et al. (2016); & Aihara et al. (2014).

The known mechanism(s) underlying ASPH’s transforming activity are the following: upregulation of ASPH is done through well-known upstream growth factor signaling pathways, such as Wnt/β-catenin, PI3K-AKT and insulin-IGF-1/IRS-1/ERK-MAPK and by hypoxia. Longato et al. (2009); Elvidge et al. (2006). ASPH overexpression in a malignancy activates Notch1 signaling by hydroxylating and directly binding to the Notch1 receptor and ligands, followed by generation of the Notch intracellular domain (NICD1), which translocates to the nucleus where it functions as part of a transcriptional complex that upregulates genes responsible for known hallmarks of cancer development and progression, such as c-Myc, MMPs and VEGF. It has been reported that other mechanisms also contribute to ASPH oncogenic properties, including inhibition of apoptosis, impairment of cell senescence, enhancement of cancer stem cell formation (Dong et al. (2015)), and dysregulation of cell cycle controlled through phosphorylation of the retinoblastoma gene (RB) (Iwagami et al. (2016)).

So, the ability to measure ASPH at an early stage of cancer has merit and is a potential game changer. This invention greatly fills the gaps in knowledge for early diagnosis, prognosis and therapy of substantial patient care and commercial importance.

ASPH Antibodies

This invention discloses the development and characterization of a unique monoclonal antibody (mAb) directed against a transmembrane protein that can be used for early diagnosis, prognosis and therapy of a broad-spectrum of human malignancies. This invention provides an antibody (herein “LRC1”) that binds to the full-length isoform of ASPH, the antibody comprising a light chain (SEQ ID NO: 11) and a heavy chain (SEQ ID NO: 10), wherein the light chain comprises a LCVR (SEQ ID NO: 9) and the heavy chain comprises a HCVR (SEQ ID NO: 8), wherein the LCVR comprises complementarity determining regions LCDR1, LCDR2, and LCDR3, and the HCVR comprises complementarity determining regions HCDR1, HCDR2, and HCDR3, wherein LCDR1 is SEQ ID NO: 5, LCDR2 is SEQ ID NO: 6, LCDR3 is SEQ ID NO: 7, HCDR1 is SEQ ID NO: 2, HCDR2 is SEQ ID NO: 3, and HCDR3 is SEQ ID NO: 4. The unique amino acid sequence of the cloned LRC1 monoclonal antibody has been determined and is provided in TABLE 2.

TABLE 2

LRC1 amino acid sequence

| SEQ ID NO: | Identity | Sequence |
|---|---|---|
| 2 | Heavy Chain-CDR1 | RYAMP |
| 3 | Heavy Chain-CDR2 | TISSGGSYTYYPDSVKG |
| 4 | Heavy Chain-CDR3 | QGNYYGSSHLYYAMDY |
| 5 | Light Chain-CDR1 | TLNSQHRAYTIE |
| 6 | Light Chain-CDR2 | GSHSTGD |
| 7 | Light Chain-CDR3 | GVGDTIKEQFVYV |

TABLE 2-continued

| LRC1 amino acid sequence | | |
|---|---|---|
| SEQ ID NO: | Identity | Sequence |
| 8 | Heavy Chain Variable Region (HCVR) | MKLWLSWVFLALILKGVQCEVQLVESGGGLVKPGGSLKFSCAASGF TFSRYAMPWVRQTPEKRLEWVATISSGGSYTYYPDSVKGRLTISRD NAKNTLYLQMSSLRSEDTAMYYCARQGNYYGSSHLYYAMDYWGQGT SVTVSS |
| 9 | Light Chain Variable Region (LCVR) | MAWIPLLFFVLHCSGSFSQLVLTQSSSASFSLGASAKLTCTLNSQH RAYTIEWYQQQPLKPPKYVMELKKDGSHSTGDGIPDRFSGSSSGAD RYLSISNIQPEDEAIYICGVGDTIKEQFVYVFGGGTKVTVL |
| 10 | Heavy Chain (144 aa) | Signal peptide-FR1-**CDR1**-FR2-**CDR2**-FR3-**CDR3**-FR4 MKLWLSWVFLALILKGVQCEVQLVESGGGLVKPGGSLKFSCAASGF TFS**RYAMP**WVRQTPEKRLEWVA**TISSGGSYTYYPDSVKG**RLTISRD NAKNTLYLQMSSLRSEDTAMYYCAR**QGNYYGSSHLYYAMDY**WGQGT SVTVSS |
| 11 | Light Chain (133 aa) | Signal peptide-FR1-**CDR1**-FR2-**CDR2**-FR3-**CDR3**-FR4 MAWIPLLFFVLHCSGSFSQLVLTQSSSASFSLGASAKLTC**TLNSQH RAYTIE**WYQQQPLKPPKYVMELKKD**GSHSTGD**GIPDRFSGSSSGAD RYLSISNIQPEDEAIYIC**GVGDTIKEQFVYV**FGGGTKVTVL |

The unique nucleic acid sequence of the cloned LRC1 monoclonal antibody has been determined and is provided in TABLE 3.

TABLE 3

| LRC1 nucleic acid sequence | | |
|---|---|---|
| SEQ ID NO: | Identity | Sequence |
| 12 | Heavy Chain-CDR1 | AGGTATGCCATGCCT |
| 13 | Heavy Chain-CDR2 | ACCATTAGTAGTGGTGGTAGTTACACCTACTATCCAGACAGTGTGA AGGGT |
| 14 | Heavy Chain-CDR3 | CAGGGAAATTACTACGGTAGTAGCCACCTTTACTATGCTATGGACT AC |
| 15 | Light Chain-CDR1 | ACCTTGAATAGTCAACACCGTGCGTACACCATTGAA |
| 16 | Light Chain-CDR2 | GGAAGCCACAGTACAGGTGAT |
| 17 | Light Chain-CDR3 | GGTGTGGGTGATACAATTAAGGAACAATTTGTGTATGTT |
| 18 | Heavy Chain Variable Region (HCVR) | GAAGTGCAGCTGGTGGAGTCTGGGGGAGGCTTAGTGAAGCCTGGAG GGTCCCTGAAATTCTCCTGTGCAGCCTCTGGATTCACTTTCAGTAG GTATGCCATGCCTTGGGTTCGCCAGACTCCGGAGAAGAGGCTGGAG TGGGTCGCAACCATTAGTAGTGGTGGTAGTTACACCTACTATCCAG ACAGTGTGAAGGGTCGACTCACCATCTCCAGAGACAATGCCAAGAA CACCCTGTACCTGCAAATGAGCAGTCTGAGGTCTGAGGACACGGCC ATGTATTACTGTGCAAGACAGGGAAATTACTACGGTAGTAGCCACC TTTACTATGCTATGGACTACTGGGGTCAAGGAACCTCAGTCACCGT CTCCTCA |
| 19 | Light Chain Variable Region (LCVR) | CAACTTGTGCTCACTCAGTCATCTTCAGCCTCTTTCTCCCTGGGAG CCTCAGCAAAACTCACGTGCACCTTGAATAGTCAACACCGTGCGTA CACCATTGAATGGTATCAGCAACAGCCACTCAAGCCTCCTAAGTAT GTGATGGAACTTAAGAAAGATGGAAGCCACAGTACAGGTGATGGGA TTCCTGATCGCTTCTCTGGATCCAGTTCTGGTGCTGATCGCTACCT TAGCATTTCCAACATCCAGCCTGAAGATGAAGCAATATACATCTGT GGTGTGGGTGATACAATTAAGGAACAATTTGTGTATGTTTTCGGCG GTGGAACCAAGGTCACTGTCCTA |
| 20 | Heavy Chain (432 bp) | Signal sequence-FR1-**CDR1**-FR2-**CDR2**-FR3-**CDR3**-FR4 ATGAAGTTGTGGTTAAGCTGGGTTTTCCTTGCCCTCATTTTAAAAG GTGTCCAGTGTGAAGTGCAGCTGGTGGAGTCTGGGGGAGGCTTAGT GAAGCCTGGAGGGTCCCTGAAATTCTCCTGTGCAGCCTCTGGATTC ACTTTCAGT**AGGTATGCCATGCCT**TGGGTTCGCCAGACTCCGGAGA |

TABLE 3-continued

| SEQ ID NO: | Identity | Sequence |
|---|---|---|
| | | LRC1 nucleic acid sequence |
| | | AGAGGCTGGAGTGGGTCGCA**ACCATTAGTAGTGGTGGTAGTTACAC**<br>**CTACTATCCAGACAGTGTGAAGGGT**CGACTCACCATCTCCAGAGAC<br>AATGCCAAGAACACCCTGTACCTGCAAATGAGCAGTCTGAGGTCTG<br>AGGACACGGCCATGTATTACTGTGCAAGA**CAGGGAAATTACTACGG**<br>**TAGTAGCCACCTTTACTATGCTATGGACTAC**TGGGGTCAAGGAACC<br>TCAGTCACCGTCTCCTCA |
| 21 | Light Chain (399 bp) | Signal sequence-FR1-**CDR1**-FR2-**CDR2**-FR3-**CDR3**-FR4<br>ATGGCCTGGATTCCTCTCTTATTCTTTGTTCTTCATTGCTCAGGTT<br>CTTTCTCCCAACTTGTGCTCACTCAGTCATCTTCAGCCTCTTTCTC<br>CCTGGGAGCCTCAGCAAAACTCACGTGC**ACCTTGAATAGTCAACAC**<br>**CGTGCGTACACCATTGAA**TGGTATCAGCAACAGCCACTCAAGCCTC<br>CTAAGTATGTGATGGAACTTAAGAAAGAT**GGAAGCCACAGTACAGG**<br>**TGAT**GGGATTCCTGATCGCTTCTCTGGATCCAGTTCTGGTGCTGAT<br>CGCTACCTTAGCATTTCCAACATCCAGCCTGAAGATGAAGCAATAT<br>ACATCTGT**GGTGTGGGTGATACAATTAAGGAACAATTTGTGTATGT**<br>**T**TTCGGCGGTGGAACCAAGGTCACTGTCCTA |

Figure 2:
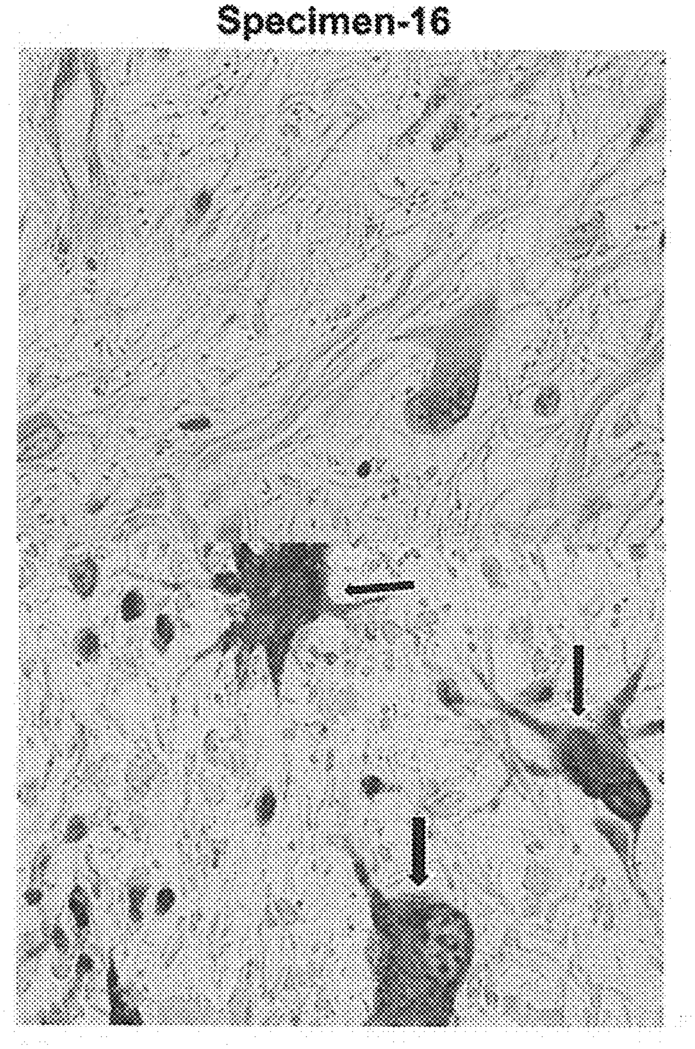
FIG. 2 shows representative examples of ASPH expression in liposarcomas as shown by IHC using LRC1.
Figure 3:
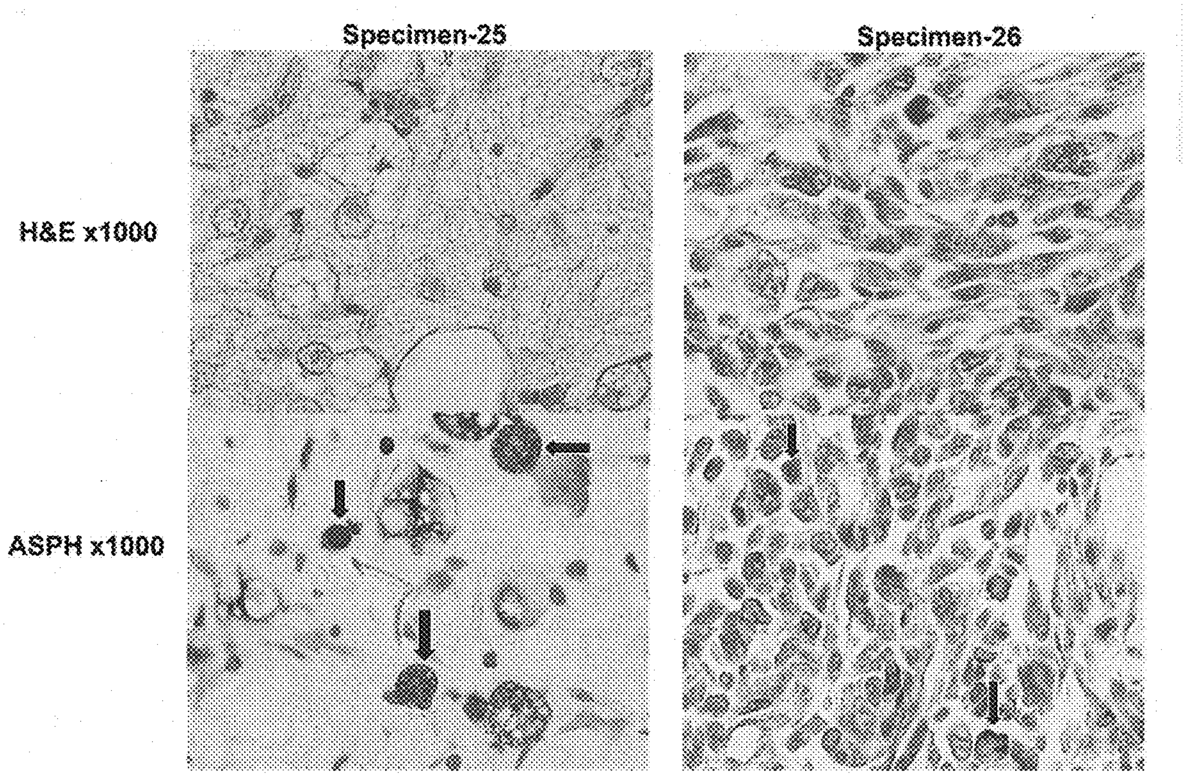
FIG. 3 shows representative examples of ASPH expression in retroperitoneal sarcomas as shown by IHC using LRC1.
Figure 4:
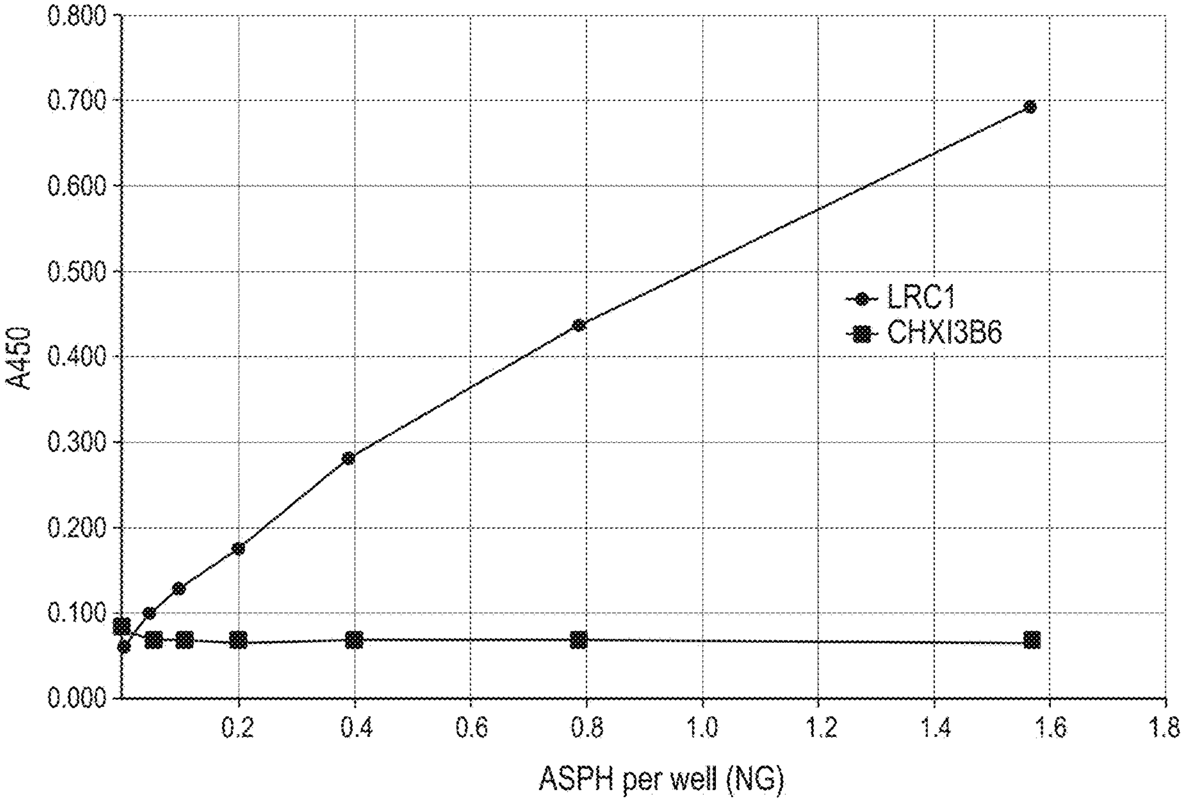
FIG. 4 provides a line graph describing that LRC1 binding to ASPH represents immunodetection of the full-length Isoform 1 of ASPH protein bound to a solid phase support. The upper line represents the OD values of protein per well and the assay can detect as little as 25 pg of ASPH in a 2-hour assay. The lower line is a control mAb of the same isotype. In this assay, the LRC1 mAb is labeled with biotin and binding to ASPH on the plate which is detected by an ELISA format.
Figure 5:
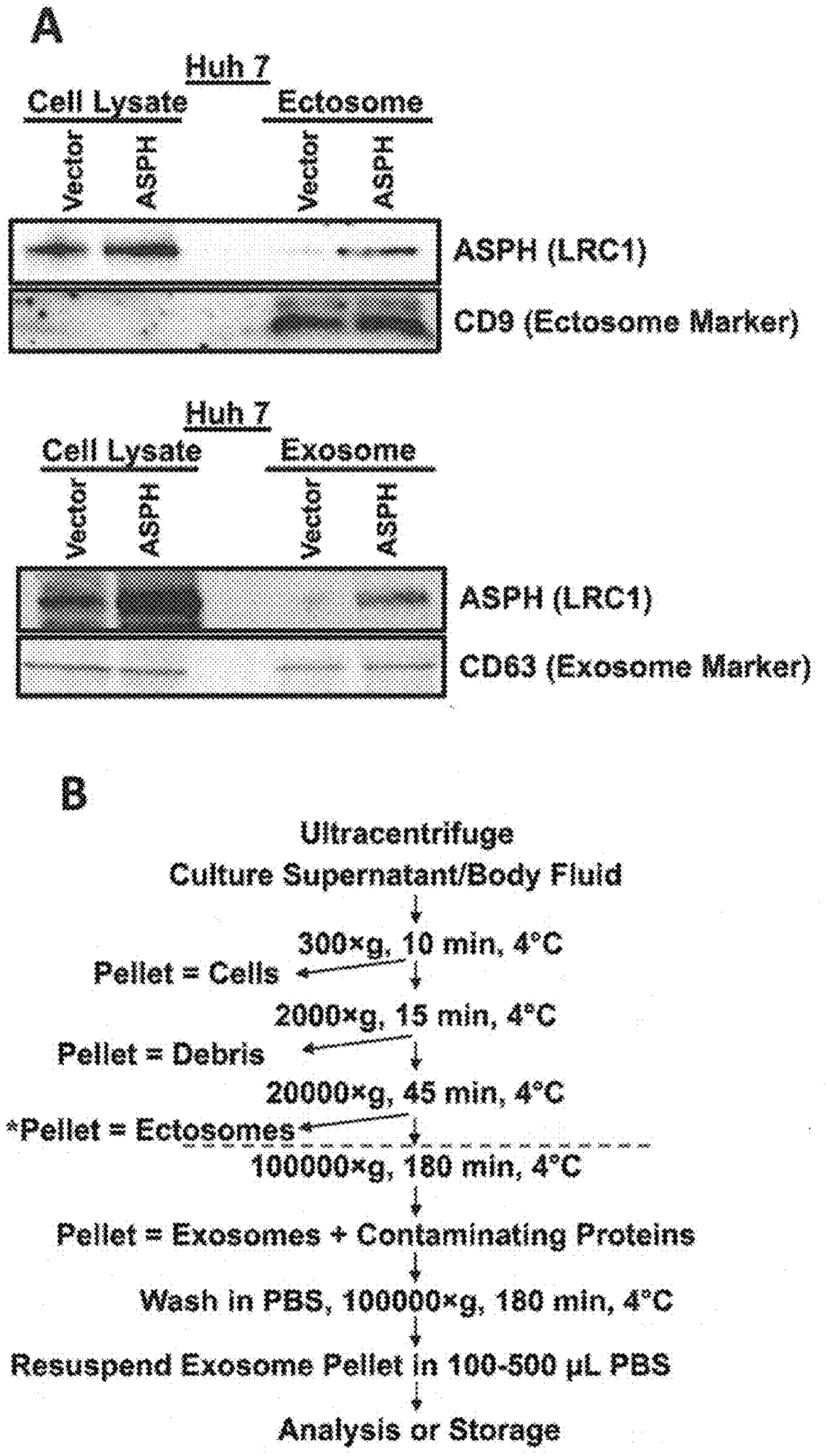
FIG. 5 shows the detection of the LRC1 epitope on the cell surface of ectosomes and exosomes derived from tissue culture of a human hepatocellular carcinoma (HCC) cell line (Huh7). Comparisons were made between cell lysate detection in ectosomes (upper Panel A), and exosomes (lower Panel A) as purified according to the procedure outlined in Panel B. Antibody CD9 was selected as the ectosome marker and CD63 as the exosome marker. There is endogenous expression in Huh7 cell culture supernatant transfected with an empty vector and the levels are increased when transfected with a full-length spliced variant 1 construct of human ASPH as indicated by increased cellular levels by Western blot analysis. Note that the LRC1 ASPH epitope is expressed on both ectosomes and exosomes following transfection in Huh7 cells.
Figure 6:
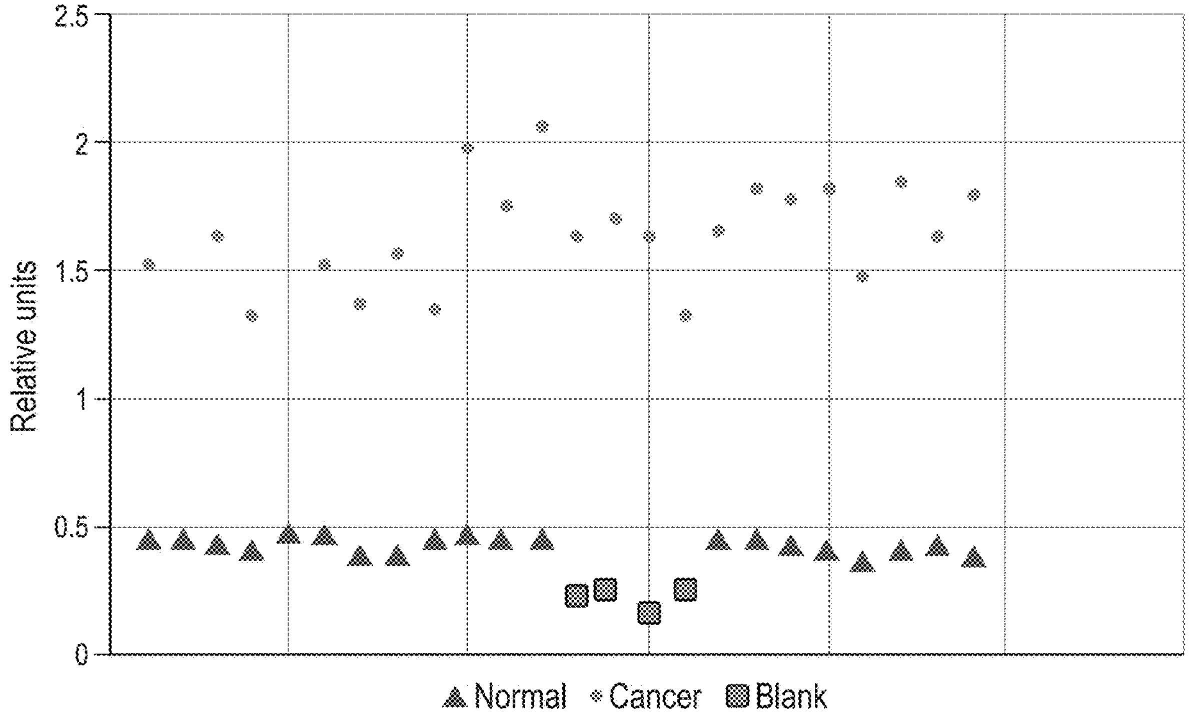
FIG. 6 shows the measurement of the LRC1 single antibody detection of the full-length isoform of ASPH (splice variant 1) in cancer serum compared to normal controls. The pooled cancer serum samples are from prostate, breast, lung and colon origin at various stages. Approximately 25 μL of serum samples was used for each test. Pooled normal serum samples were derived from five healthy subjects (25 μL per run). There were 22 cancer runs (circles), 20 normal runs (triangles), and four runs with blank buffer solutions (squares).
Figure 7:
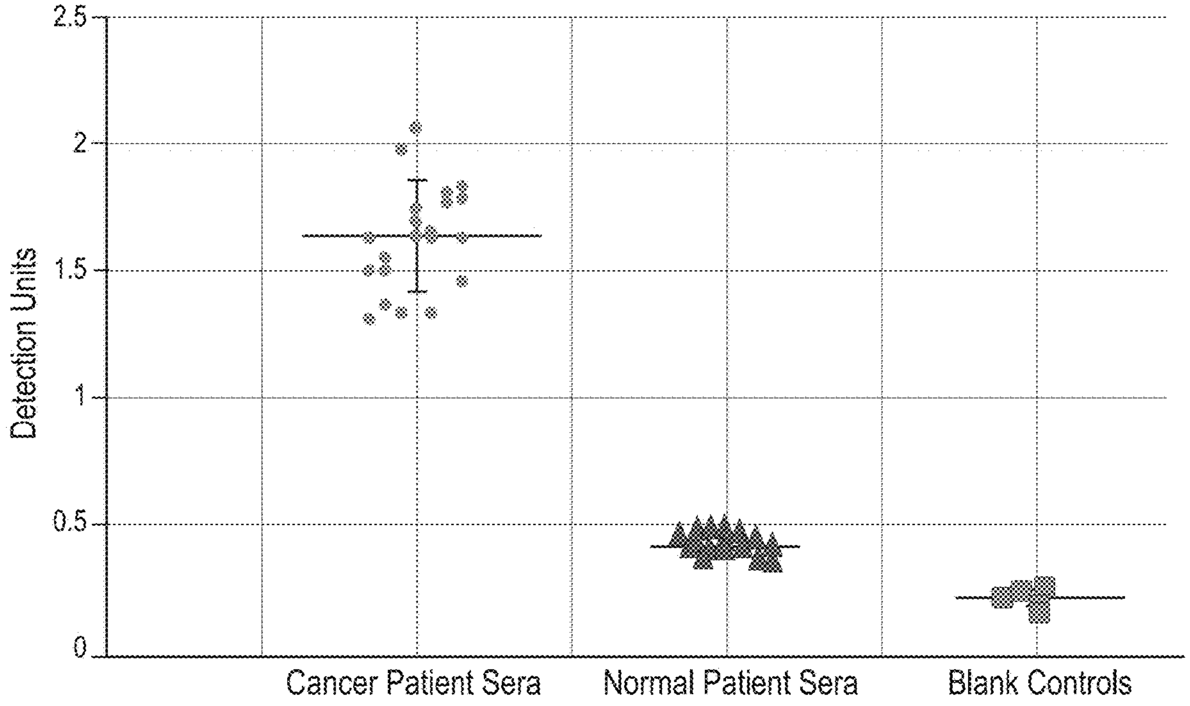
FIG. 7 shows the early detection of cancer in liquid biopsies. A composite graph showing the clear separation of cancer patients ASPH levels from normal controls which suggests that it could be used as a screening assay for the early detection of cancer. This is an automated platform that uses lateral flow and microfluidic based approaches which includes both optical and electronic sensing.

Monoclonal antibodies have previously been produced against the ASPH protein but only LRC1 antibodies among several hundred such antibodies recognize a unique 6 amino acid epitope and have these surprising, unexpected and highly desirable properties. The LRC1 antibodies of this invention bind to a polypeptide within the full length ASPH isoform amino acid sequence determine to be NPVEDS (SEQ ID NO: 24, residues 286-291 of SEQ ID NO: 1). The LRC1 antibodies of this invention provide improved sensitivity and specificity of assays designed for detection of early tumor formation (including pre-malignant lesions and in situ malignancies) using liquid biopsies. This is due to the unique and surprising properties of LRC1 antibodies which are: (1) recognition of the full-length isoform of ASPH that has transforming activity when overexpressed in cells (data shown in TABLE 4 and TABLE 5); (2) for the first time, recognition of ASPH expression in tumors derived from the mesoderm such as sarcomas (data shown in FIGS. 1-3); (3) detection of as little as 25 μg of full length ASPH protein (antigen) bound to a solid phase support (data shown in FIG. 4); (4) detection of the ASPH presence in cancer-cell derived extracellular vesicles (ectosomes and exosomes) as a companion diagnostic test of a malignancy (data shown in FIG. 5); (5) a single LRC1 mAb-based immunoassay has been developed as a highly sensitive technique for the early cancer diagnosis using 15-25 μL of blood derived from a finger prick (data shown in FIGS. 6-7) only involving the use of LRC1 mAb and using lateral flow and micro fluidic analysis that is digitally and optically controlled and automated; (6) the exact 6 amino acid epitope (i.e., NPVEDS (SEQ ID NO: 24)) to which LRC1 binds on the full-length oncogenic protein has been defined (shadowed in Table 1) and is expressed on the cell surface of tumor cells and ASPH positive cancer-cell derived extracellular vesicles; and (7) the unique amino acid and nucleic acid sequences of the LRC1 mAb have been determined (provided in Table 2 and Table 3, respectively). Taken together, the many embodiments of this invention greatly advance the capability for early detection and prognosis of cancer and can be used as a targeting agent to deliver a cytotoxic "payload" or to recruit cytotoxic immune cells to ASPH expressing tumors. Using a single antibody, with this degree of immunoreactivity in tumors derived from the endoderm, mesoderm and ectoderm, is unprecedented and pertains to human oncogenesis.

TABLE 4

Percent of human tumors studied by immunohistochemistry using the LRC1 monoclonal antibody that express ASPH

| Tumor Tissue Type | N | % Positive | Source |
|---|---|---|---|
| Hepatocellular carcinoma | 87 | 92 | PRC + USA |
| Cholangiocarcinoma | 27 | 100 | USA |
| Gallbladder cancer | 66 | 100 | PRC |
| Non-small cell lung cancer | 304 | 82 | PRC + USA |
| Breast cancer | 275 | 91 | PRC + USA |
| Gastric cancer | 51 | 80 | PRC |
| Pancreatic cancer | 275 | 97 | PRC + USA |
| Soft tissue sarcoma | 36 | 84 | PRC |
| Osteosarcoma | 18 | 80 | USA |
| Colon cancer | 41 | 80 | PRC + USA |
| Renal cancer | 49 | 83 | PRC |
| Myeloid leukemia | 79 | 88 | PRC |
| Prostate cancer | 46 | 96 | USA |
| Glioblastoma | 15 | 98 | USA |
| Head and Neck cancer | 22 | 91 | USA |
| Lymphoid leukemia | 80 | 80 | PRC |
| Normal bone marrow | 130 | 0 | PRC |

Abbreviations: PRC, People's Republic of China; USA, the United States.

TABLE 5

Percent of human tumors studied by immunohistochemistry using the LRC1 monoclonal antibody that express ASPH

| Tumor Tissue Type | N | % Positive | Source |
|---|---|---|---|
| Soft tissue sarcoma | 36 | 84 | PRC |
| Osteosarcoma | 18 | 80 | USA |
| Chondrosarcoma | 10 | 100 | USA |

Abbreviations: PRC, People's Republic of China; USA, the United States.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art recognize. While method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to use the compositions, functions and concepts of the above references and application to provide yet further embodiments of the disclosure. Due to biological functional equivalency considerations, some changes can be made in protein amino acid sequence or structure without affecting the biological or chemical action in kind or amount. These and other changes can be made to the disclosure, given the detailed description. All such changes are intended to be included within the scope of the appended claims.

Specific elements of any of the foregoing embodiments can be combined or substituted for elements in other embodiments. While advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following additional numbered embodiments which in no way should be construed as being further limiting.

1. An antibody that binds to the full-length isoform of aspartate beta-hydroxylase (ASPH) comprising a light chain and a heavy chain, wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, wherein LCDR1 consists of amino acid sequence SEQ ID NO: 5, LCDR2 consists of amino acid sequence SEQ ID NO: 6, LCDR3 consists of amino acid sequence SEQ ID NO: 7, HCDR1 consists of amino acid sequence SEQ ID NO: 2, HCDR2 consists of amino acid sequence SEQ ID NO: 3, and HCDR3 consists of amino acid sequence SEQ ID NO: 4.
2. An antibody that binds to the full-length isoform of ASPH comprising a light chain and a heavy chain, wherein the light chain comprises an LCVR, and the heavy chain comprises an HCVR, wherein the LCVR comprises amino acid sequence SEQ ID NO: 9 and the HCVR comprises amino acid sequence SEQ ID NO: 8.
3. An antibody that binds to the full-length isoform of ASPH comprising a light chain and a heavy chain, wherein the light chain comprises amino acid sequence SEQ ID NO: 11 and the heavy chain comprises amino acid sequence SEQ ID NO: 10.
4. An antibody that binds to the full-length isoform of ASPH comprising two light chains and two heavy chains, wherein each light chain comprises amino acid sequence SEQ ID NO: 11 and each heavy chain comprises SEQ ID NO: 10.
5. A DNA molecule comprising a polynucleotide sequence encoding a light chain polypeptide having the amino acid sequence SEQ ID NO: 11.
6. A DNA molecule comprising a polynucleotide sequence encoding a heavy chain polypeptide having the amino acid sequence SEQ ID NO: 10.
7. A recombinant host cell comprising the DNA molecule of embodiment 5 and the DNA molecule of embodiment 6, which cell is capable of expressing an antibody comprising a heavy chain and a light chain, wherein the amino acid sequence of the heavy chain is SEQ ID NO: 10 and the amino acid sequence of the light chain is SEQ ID NO: 11.
8. A process for producing an antibody that binds to human ASPH comprising a heavy chain and a light chain, wherein the heavy chain comprises amino acid sequence SEQ ID NO: 10 and the light chain comprises the amino acid sequence of SEQ ID NO: 11, said process comprising the steps of: (a) cultivating a recombinant host cell of embodiment 7, under conditions such that said antibody is expressed; and (b) recovering from said host cell the expressed antibody.
9. An antibody produced by the process of embodiment 8.
10. A pharmaceutical composition comprising an antibody of any one of embodiments 1-4 and one or more pharmaceutically acceptable carriers, diluents or excipients.
11. An assay comprising:
(i) measuring, in a sample obtained from a subject, a level of ASPH, wherein said measuring comprises incubating the sample in an article with an immobilized antibody of any one of embodiments 1-4;
(ii) comparing the level of ASPH with a reference level; and
(iii) identifying the subject as:
(a) having a malignant neoplasm if the level of ASPH is above the reference level; or
(b) not having a malignant neoplasm if the level of ASPH is at or below the reference level.
12. The assay of embodiment 11, wherein the biological sample is serum, the detected level of ASPH is compared with the reference level in a subject's serum.
13. The assay of any one of embodiments 11-12, wherein when the level of ASPH is above the reference level, the assay further comprises providing a confirming diagnosis, and treatment appropriate for treating the malignant neoplasm.
14. The assay of embodiment 13, wherein the treatment comprises administering to the subject a composition comprising a therapeutically effective amount of an antibody of any one of embodiments 1-4 linked to a cytotoxic agent.
15. The assay of embodiment 13, wherein the confirming diagnosis is obtained using a diagnostic tool selected from the group consisting of: imaging, endoscopy, biopsy, histology, cytology, and pathology.
16. The assay of any one of embodiments 11-15, wherein the malignant neoplasm is selected from the group consisting of: head and neck cancer, thyroid cancer, thymus cancer, non-small cell lung cancer, esophageal cancer, gastric cancer, hepatocellular carcinoma, gallbladder cancer, cholangiocarcinoma, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, and lymphoid leukemia multiple myeloma, lymphoma, primary malignant CNS neoplasms of both neuronal and glial cell origin and metastatic CNS neoplasms, skin cancer, and melanoma.
17. A method of monitoring treatment progress in a subject having a malignant neoplasm, the method comprising:
(i) measuring, at a first time point, a first level of ASPH in a first sample obtained from the subject, wherein said measuring comprises incubating the first sample in an article with an immobilized antibody of any one of embodiments 1-4;
(ii) administering to the subject a therapeutic agent or approach for treating the malignant neoplasm;

(iii) measuring, at a second time point, a second level of ASPH in a second sample obtained from the subject, wherein said measuring comprises incubating the second sample in an article with an immobilized antibody of any one of embodiments 1-4; wherein a second level measurement significantly lower than the first level measurement indicates that the therapeutic agent or approach is effective.

18. A method of treating a malignant neoplasm in a subject, the method comprising administering a therapeutically effective amount of an antibody and derivatives of any one of embodiments 1-4 linked to a cytotoxic agent to the subject.

19. The method of any one of embodiments 17-18, wherein the malignant neoplasm is selected from the group consisting of, but not limited to: head and neck cancer, thyroid cancer, thymus cancer, non-small cell lung cancer, esophageal cancer, gastric cancer, hepatocellular carcinoma, gallbladder cancer, cholangiocarcinoma, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, and lymphoid leukemia multiple myeloma, lymphoma, primary malignant CNS neoplasms of both neuronal and glial cell origin and metastatic CNS neoplasms, skin cancer, and melanoma.

20. A kit for detecting a malignant tumor cell comprising an antibody or an ASPH-biding fragment and derivates, thereof, wherein said antibody or ASPH-biding fragment and a derivative bind to residues 286-291 of SEQ ID NO: 1.

21. The kit of embodiment 20, further comprising a means for detecting binding of said antibody and a derivate to said malignant tumor cell.

22. The kit of embodiment 22, wherein said means is a detectable maker.

23. The kit of embodiment 22, wherein said detectable marker is a radioactive compound.

24. The kit of embodiment 22, wherein said detectable marker is $Gd^{+++}$ or $Fe^{++}$.

25. The kit of any one of embodiments 20-24, wherein the malignant tumor cell is from a malignant neoplasm selected from the group consisting of: head and neck cancer, thyroid cancer, thymus cancer, non-small cell lung cancer, esophageal cancer, gastric cancer, hepatocellular carcinoma, gallbladder cancer, cholangiocarcinoma, pancreatic cancer, colon and rectum cancer, renal cancer, prostate cancer, breast cancer, ovarian, fallopian tube and cervical cancer, soft tissue sarcoma, osteosarcoma, chondrosarcoma, malignant mesothelioma, myeloid leukemia, and lymphoid leukemia multiple myeloma, lymphoma, primary malignant CNS neoplasms of both neuronal and glial cell origin and metastatic CNS neoplasms, skin cancer, and melanoma.

Although methods and materials similar or equivalent to those described herein can be used in the practice or testing of this disclosure, suitable methods, protocols and materials are described below.

REFERENCES

Aihara et al. (2014). "A cell surface beta hydroxylase is a biomarker and therapeutic target for hepatocellular carcinoma." Hepatology 60(4):1302-1313.

Berend et al. (1998). Association between ratio of matrix metalloproteinase-1 to tissue inhibitor of metalloproteinase-1 and local recurrence, metastasis, and survival in human chondrosarcoma. J Bone Joint Surg Am 80: 11 17.

Bray et al. (2018). "2018: GLOBOCAN estimates of incidence and mortality worldwide for 36 cancers in 185 countries." CA Cancer J. Clin. 68: 394-424.

Chothia & Lesk (1987). "Canonical structures for the hypervariable regions of immunoglobulins." J. Mol. Biol. 196(4): 901-917.

Chothia et al. (1989). "Conformations of immunoglobulin hypervariable regions." Nature 342(6252): 877-883.

Coyle et al. (2017). "Genetic mutations and epigenetic modifications: driving cancer and informing precision medicine." Biomed. Res. Int. 2017: 9620870.

Current Protocols in Immunology (CPI) (2003). John E. Coligan, ADA M Kruisbeek, David H Margulies, Ethan M Shevach, Warren Strobe, (eds.) John Wiley and Sons, Inc. (ISBN 0471142735, 9780471142737).

Current Protocols in Molecular Biology (CPMB), (2014). Frederick M. Ausubel (ed.), John Wiley and Sons (ISBN 047150338X, 9780471503385).

Current Protocols in Protein Science (CPPS), (2005). John E. Coligan (ed.), John Wiley and Sons, Inc.

Davis et al. (2012). Basic Methods in Molecular Biology, Elsevier Science Publishing, Inc., New York, USA (ISBN 044460149X).

Dong et al. (2015). "Aspartate beta-Hydroxylase expression promotes a malignant pancreatic cellular phenotype." Oncotarget 6: 1231 1248.

Elvidge et al. (2006). "Concordant regulation of gene expression by hypoxia and 2-oxoglutarate-dependent dioxygenase inhibition: the role of HIF-1alpha, HIF-2alpha, and other pathways." J. Biol. Chem. 281: 15215 15226.

Engin et al. (2009). "Notch signaling contributes to the pathogenesis of human osteosarcomas." Hum. Mol. Genet. 18: 1464 1470.

Fang et al. (2000). "Matrix metalloproteinase-2 is required for the switch to the angiogenic phenotype in a tumor model." Proc. Natl. Acad. Sci. U.S.A 97: 3884 3889.

Hou et al. (2011). "WISP-1 increases MMP-2 expression and cell motility in human chondrosarcoma cells." Biochem. Pharmacol. 81: 1286 1295.

Huang et al. (2016). "Anti-Tumor Effects of Second Generation beta-Hydroxylase Inhibitors on Cholangiocarcinoma Development and Progression." PLOS One 11: e0150336.

Immunology (2006). Werner Luttmann, published by Elsevier.

Isselbacher et al. (1996). Harrison's Principles of Internal Medicine, 13 ed., 1814-1882.

Iwagami et al. (2016). "Aspartate beta-hydroxylase modulates cellular senescence through glycogen synthase kinase 3beta in hepatocellular carcinoma." Hepatology 63: 1213 1226.

Janeway's Immunobiology (2014). Kenneth Murphy, Allan Mowat, Casey Weaver (eds.), Taylor & Francis Limited, (ISBN 0815345305, 9780815345305).

Jawad et al. (2010). "Matrix metalloproteinase 1: role in sarcoma biology." PLOS One 5: e14250.

Jia et al. (1992). "cDNA cloning and expression of bovine aspartyl (asparaginyl) beta-hydroxylase." J. Biol. Chem. 267: 14322-14327.

Kabat et al. (1987) and (1991). Sequences Of Proteins of Immunological Interest. (National Institutes of Health, Bethesda, MD, USA)

Kabat et al. (1991). Sequences of Proteins of Immunological Interest. Fifth Edition, U.S. Department of Health and Human Services, NIH Publication No. 91 3242.

Korioth et al. (1994). "Cloning and characterization of the human gene encoding aspartyl beta-hydroxylase." Gene 150: 395-399.

Laboratory Methods in Enzymology: DNA, (2013). Jon Lorsch (ed.) Elsevier (ISBN 0124199542).

Lavaissiere et al. (1996). "Overexpression of human aspartyl(asparaginyl)beta-hydroxylase in hepatocellular carcinoma and cholangiocarcinoma." The Journal of Clinical Investigation 98: 1313 1323.

Lewin's Genes XI, (2014). published by Jones & Bartlett Publishers (ISBN-1449659055).

Longato et al. (2009). "Overexpression of insulin receptor substrate-1 and hepatitis Bx genes causes premalignant alterations in the liver." Hepatology 49: 1935 1943.

MacCallum et al. (1996). "Antibody-antigen interactions: contact analysis and binding site topography." J. Mol. Biol. 262(5): 732-745.

Michael Richard Green & Joseph Sambrook, (2012). Molecular Cloning: A Laboratory Manual, 4th ed., Cold Spring Harbor Laboratory Press, Cold Spring Harbor, N.Y., USA (ISBN 1936113414).

Molecular Biology and Biotechnology: A Comprehensive Desk Reference (1995). Robert A. Meyers (ed.), published by VCH Publishers, Inc. (ISBN 1-56081-569-8).

Padlan et al. (1995). "Identification of specificity-determining residues in antibodies." FASEB J. 9(1): 133-139.

Patel et al. (2014). "Mutations in ASPH cause facial dysmorphism, lens dislocation, anterior-segment abnormalities, and spontaneous filtering blebs, or Traboulsi syndrome." Am. J. Hum. Genet. 94: 755 759.

Soderstrom et al. (2001). "Expression of matrix metalloproteinases and tissue inhibitors of metalloproteinases in human chondrosarcomas." APMIS 109: 305 315.

Tang et al. (2011). "IL-6 increases MMP-13 expression and motility in human chondrosarcoma cells." J. Biol. Chem. 286: 11056 11066.

The Encyclopedia of Molecular Cell Biology and Molecular Medicine, Robert S. Porter et al. (eds.), published by Blackwell Science Ltd., 1999-2012 (ISBN 9783527600908).

The Merck Manual of Diagnosis and Therapy (2011). 19th Edition, published by Merck Sharp & Dohme Corp., (ISBN 978-0-911910-19-3).

Uria et al. (1998). "Collagenase-3 (MMP-13) expression in chondrosarcoma cells and its regulation by basic fibroblast growth factor." Am. J. Pathol. 153: 91 101.

Xu et al. (2016). "Metastasis-associated lung adenocarcinoma transcript 1 promotes the proliferation of chondrosarcoma cell via activating Notch-1 signaling pathway." Onco. Targets Ther. 9: 2143 2151.

Zhou et al. (2018). "Prognostic significance of matrix metalloproteinase 9 expression in osteosarcoma: A meta-analysis of 16 studies." Medicine (Baltimore) 97: e13051.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of this application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice this aspects and embodiments. These aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following claims.

SEQUENCE LISTING

```
Sequence total quantity: 24
SEQ ID NO: 1            moltype = AA  length = 758
FEATURE                 Location/Qualifiers
source                  1..758
                        mol_type = protein
                        organism = Homo sapiens
SEQUENCE: 1
MAQRKNAKSS GNSSSSGSGS GSTSAGSSSP GARRETKHGG HKNGRKGGLS GTSFFTWFMV  60
IALLGVWTSV AVVWFDLVDY EEVLGKLGIY DADGDGDFDV DDAKVLLGLK ERSTSEPAVP  120
PEEAEPHTEP EEQVPVEAEP QNIEDEAKEQ IQSLLHEMVH AEHVEGEDLQ QEDGPTGEPQ  180
QEDDEFLMAT DVDDRFETLE PEVSHEETEH SYHVEETVSQ DCNQDMEEMM SEQENPDSSE  240
PVVEDERLHH DTDDVTYQVY EEQAVYEPLE NEGIEITEVT APPEDNPVED SQVIVEEVSI  300
FPVEEQQEVP PETNRKTDDP EQKAKVKKKK PKLLNKFDKT IKAELDAAEK LRKRGKIEEA  360
VNAFKELVRK YPQSPRARYG KAQCEDDLAE KRRSNEVLRG AIETYQEVAS LPDVPADLLK  420
LSLKRRSDRQ QFLGHMRGSL LTLQRLVQLF PNDTSLKNDL GVGYLLIGDN DNAKKVYEEV  480
LSVTPNDGFA KVHYGFILKA QNKIAESIPY LKEGIESGDP GTDDGRFYFH LGDAMQRVGN  540
KEAYKWYELG HKRGHFASVW QRSLYNVNGL KAQPWWTPKE TGYTELVKSL ERNWKLIRDE  600
GLAVMDKAKG LFLPEDENLR EKGDWSQFTL WQQGRRNENA CKGAPKTCTL LEKFPETTGC  660
```

```
RRGQIKYSIM HPGTHVWPHT GPTNCRLRMH LGLVIPKEGC KIRCANETRT WEEGKVLIFD  720
DSFEHEVWQD ASSFRLIFIV DVWHPELTPQ QRRSLPAI                          758

SEQ ID NO: 2            moltype = AA  length = 5
FEATURE                 Location/Qualifiers
source                  1..5
                        mol_type = protein
                        organism = synthetic construct
SEQUENCE: 2
RYAMP                                                              5

SEQ ID NO: 3            moltype = AA  length = 17
FEATURE                 Location/Qualifiers
source                  1..17
                        mol_type = protein
                        organism = synthetic construct
SEQUENCE: 3
TISSGGSYTY YPDSVKG                                                 17

SEQ ID NO: 4            moltype = AA  length = 16
FEATURE                 Location/Qualifiers
source                  1..16
                        mol_type = protein
                        organism = synthetic construct
SEQUENCE: 4
QGNYYGSSHL YYAMDY                                                  16

SEQ ID NO: 5            moltype = AA  length = 12
FEATURE                 Location/Qualifiers
source                  1..12
                        mol_type = protein
                        organism = synthetic construct
SEQUENCE: 5
TLNSQHRAYT IE                                                      12

SEQ ID NO: 6            moltype = AA  length = 7
FEATURE                 Location/Qualifiers
source                  1..7
                        mol_type = protein
                        organism = synthetic construct
SEQUENCE: 6
GSHSTGD                                                            7

SEQ ID NO: 7            moltype = AA  length = 13
FEATURE                 Location/Qualifiers
source                  1..13
                        mol_type = protein
                        organism = synthetic construct
SEQUENCE: 7
GVGDTIKEQF VYV                                                     13

SEQ ID NO: 8            moltype = AA  length = 144
FEATURE                 Location/Qualifiers
source                  1..144
                        mol_type = protein
                        organism = synthetic construct
SEQUENCE: 8
MKLWLSWVFL ALILKGVQCE VQLVESGGGL VKPGGSLKFS CAASGFTFSR YAMPWVRQTP  60
EKRLEWVATI SSGGSYTYYP DSVKGRLTIS RDNAKNTLYL QMSSLRSEDT AMYYCARQGN  120
YYGSSHLYYA MDYWGQGTSV TVSS                                         144

SEQ ID NO: 9            moltype = AA  length = 133
FEATURE                 Location/Qualifiers
source                  1..133
                        mol_type = protein
                        organism = synthetic construct
SEQUENCE: 9
MAWIPLLFFV LHCSGSFSQL VLTQSSSASF SLGASAKLTC TLNSQHRAYT IEWYQQQPLK  60
PPKYVMELKK DGSHSTGDGI PDRFSGSSSG ADRYLSISNI QPEDEAIYIC GVGDTIKEQF  120
VYVFGGGTKV TVL                                                     133

SEQ ID NO: 10           moltype = AA  length = 144
FEATURE                 Location/Qualifiers
source                  1..144
                        mol_type = protein
                        organism = synthetic construct
```

-continued

```
SEQUENCE: 10
MKLWLSWVFL ALILKGVQCE VQLVESGGGL VKPGGSLKFS CAASGFTFSR YAMPWVRQTP  60
EKRLEWVATI SSGGSYTYYP DSVKGRLTIS RDNAKNTLYL QMSSLRSEDT AMYYCARQGN  120
YYGSSHLYYA MDYWGQGTSV TVSS                                        144

SEQ ID NO: 11          moltype = AA  length = 133
FEATURE                Location/Qualifiers
source                 1..133
                       mol_type = protein
                       organism = synthetic construct
SEQUENCE: 11
MAWIPLLFFV LHCSGSFSQL VLTQSSSASF SLGASAKLTC TLNSQHRAYT IEWYQQQPLK  60
PPKYVMELKK DGSHSTGDGI PDRFSGSSSG ADRYLSISNI QPEDEAIYIC GVGDTIKEQF  120
VYVFGGGTKV TVL                                                    133

SEQ ID NO: 12          moltype = DNA  length = 15
FEATURE                Location/Qualifiers
source                 1..15
                       mol_type = other DNA
                       organism = synthetic construct
SEQUENCE: 12
aggtatgcca tgcct                                                  15

SEQ ID NO: 13          moltype = DNA  length = 51
FEATURE                Location/Qualifiers
source                 1..51
                       mol_type = other DNA
                       organism = synthetic construct
SEQUENCE: 13
accattagta gtggtggtag ttacacctac tatccagaca gtgtgaaggg t          51

SEQ ID NO: 14          moltype = DNA  length = 48
FEATURE                Location/Qualifiers
source                 1..48
                       mol_type = other DNA
                       organism = synthetic construct
SEQUENCE: 14
cagggaaatt actacggtag tagccacctt tactatgcta tggactac              48

SEQ ID NO: 15          moltype = DNA  length = 36
FEATURE                Location/Qualifiers
source                 1..36
                       mol_type = other DNA
                       organism = synthetic construct
SEQUENCE: 15
accttgaata gtcaacaccg tgcgtacacc attgaa                           36

SEQ ID NO: 16          moltype = DNA  length = 21
FEATURE                Location/Qualifiers
source                 1..21
                       mol_type = other DNA
                       organism = synthetic construct
SEQUENCE: 16
ggaagccaca gtacaggtga t                                           21

SEQ ID NO: 17          moltype = DNA  length = 39
FEATURE                Location/Qualifiers
source                 1..39
                       mol_type = other DNA
                       organism = synthetic construct
SEQUENCE: 17
ggtgtgggtg atacaattaa ggaacaattt gtgtatgtt                        39

SEQ ID NO: 18          moltype = DNA  length = 375
FEATURE                Location/Qualifiers
source                 1..375
                       mol_type = other DNA
                       organism = synthetic construct
SEQUENCE: 18
gaagtgcagc tggtggagtc tgggggaggc ttagtgaagc ctggagggtc cctgaaattc  60
tcctgtgcag cctctggatt cactttcagt aggtatgcca tgccttgggt tcgccagact  120
ccggagaaga ggctggagtg ggtcgcaacc attagtagtg gtggtagtta cacctactat  180
ccagacagtg tgaagggtcg actcaccatc tccagagaca atgccaagaa caccctgtac  240
ctgcaaatga gcagtctgag gtctgaggac acggccatgt attactgtgc aagacaggga  300
aattactacg gtagtagcca cctttactat gctatggact actggggtca aggaacctca  360
gtcaccgtct cctca                                                  375
```

-continued

```
SEQ ID NO: 19          moltype = DNA  length = 345
FEATURE                Location/Qualifiers
source                 1..345
                       mol_type = other DNA
                       organism = synthetic construct
SEQUENCE: 19
caacttgtgc tcactcagtc atcttcagcc tctttctccc tgggagcctc agcaaaactc  60
acgtgcacct tgaatagtca acaccgtgcg tacaccattg aatggtatca gcaacagcca  120
ctcaagcctc ctaagtatgt gatggaactt aagaaagatg gaagccacag tacaggtgat  180
gggattcctg atcgcttctc tggatccagt tctggtgctg atcgctacct tagcatttcc  240
aacatccagc ctgaagatga agcaatatac atctgtggtg tgggtgatac aattaaggaa  300
caatttgtgt atgttttcgg cggtggaacc aaggtcactg tccta                 345

SEQ ID NO: 20          moltype = DNA  length = 432
FEATURE                Location/Qualifiers
source                 1..432
                       mol_type = other DNA
                       organism = synthetic construct
SEQUENCE: 20
atgaagttgt ggttaagctg ggttttcctt gccctcattt taaaaggtgt ccagtgtgaa  60
gtgcagctgg tggagtctgg gggaggctta gtgaagcctg gagggtccct gaaattctcc  120
tgtgcagcct ctggattcac tttcagtagg tatgccatgc cttgggttcg ccagactccg  180
gagaagaggc tggagtgggt cgcaaccatt agtagtggtg gtagttacac ctactatcca  240
gacagtgtga agggtcgact caccatctcc agagacaatg ccaagaacac cctgtacctg  300
caaatgagca gtctgaggtc tgaggacacg gccatgtatt actgtgcaag acagggaaat  360
tactacggta gtagccacct ttactatgct atggactact ggggtcaagg aacctcagtc  420
accgtctcct ca                                                     432

SEQ ID NO: 21          moltype = DNA  length = 399
FEATURE                Location/Qualifiers
source                 1..399
                       mol_type = other DNA
                       organism = synthetic construct
SEQUENCE: 21
atggcctgga ttcctctctt attctttgtt cttcattgct caggttcttt ctcccaactt  60
gtgctcactc agtcatcttc agcctctttc tccctgggag cctcagcaaa actcacgtgc  120
accttgaata gtcaacaccg tgcgtacacc attgaatggt atcagcaaca gccactcaag  180
cctcctaagt atgtgatgga acttaagaaa gatggaagcc acagtacagg tgatgggatt  240
cctgatcgct tctctggatc cagttctggt gctgatcgct accttagcat ttccaacatc  300
cagcctgaag atgaagcaat atacatctgt ggtgtgggtg atacaattaa ggaacaattt  360
gtgtatgttt tcggcggtgg aaccaaggtc actgtccta                        399

SEQ ID NO: 22          moltype = AA  length = 5
FEATURE                Location/Qualifiers
source                 1..5
                       mol_type = protein
                       organism = synthetic construct
SEQUENCE: 22
GGGGS                                                             5

SEQ ID NO: 23          moltype = AA  length = 6
FEATURE                Location/Qualifiers
source                 1..6
                       mol_type = protein
                       organism = synthetic construct
SEQUENCE: 23
HHHHHH                                                            6

SEQ ID NO: 24          moltype = AA  length = 6
FEATURE                Location/Qualifiers
source                 1..6
                       mol_type = protein
                       organism = Homo sapiens
SEQUENCE: 24
NPVEDS                                                            6
```

What is claimed is:

1. An antibody that binds to the full-length isoform of aspartate beta-hydroxylase (ASPH) comprising a light chain and a heavy chain, wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, and wherein LCDR1 consists of amino acid sequence SEQ ID NO: 5, LCDR2 consists of amino acid sequence SEQ ID NO: 6, LCDR3 consists of amino acid sequence SEQ ID NO: 7, HCDR1 consists of amino acid sequence SEQ ID NO: 2, HCDR2 consists of amino acid sequence SEQ ID NO: 3, and HCDR3 consists of amino acid sequence SEQ ID NO: 4.

2. The antibody of claim 1, wherein the LCVR comprises amino acid sequence SEQ ID NO: 9 and the HCVR comprises amino acid sequence SEQ ID NO: 8.

3. The antibody of claim 1, wherein the light chain comprises amino acid sequence SEQ ID NO: 11 and the heavy chain comprises amino acid sequence SEQ ID NO: 10.

4. The antibody of claim 1, comprising two light chains and two heavy chains,
- wherein each light chain comprises amino acid sequence SEQ ID NO: 11 and each heavy chain comprises SEQ ID NO: 10.

5. An assay comprising:
- (i) measuring, in a biological sample obtained from a subject, a level of ASPH, wherein the measuring comprises incubating the biological sample in an article with an immobilized antibody of any one of claims 1-4;—
- (ii) comparing the level of ASPH with a reference level; and—
- (iii) identifying the subject as:—
- (a) having a malignant neoplasm if the level of ASPH is above the reference level; or—
- (b) not having a malignant neoplasm if the level of ASPH is at or below the reference level.

6. The assay of claim 5, wherein the biological sample is serum and the detected level of ASPH is compared with the reference level in a subject's serum.

7. A method of monitoring treatment progress in a subject having a malignant neoplasm, the method comprising:—
- (i) measuring, at a first time point, a first level of ASPH in a first sample obtained from the subject, wherein the measuring comprises incubating the first sample in an article with an immobilized antibody of any one of claims 1-4;—
- (ii) administering to the subject a therapeutic agent or approach for treating the malignant neoplasm;—
- (iii) measuring, at a second time point, a second level of ASPH in a second sample obtained from the subject, wherein the measuring comprises incubating the second sample in an article with the immobilized antibody used in step (i);
- wherein a second level measurement significantly lower than the first level measurement indicates that the therapeutic agent or approach is effective.

8. A method of treating a malignant neoplasm in a subject, the method comprising administering a therapeutically effective amount of an antibody of any one of claims 1-4 linked to a cytotoxic agent to the subject.

* * * * *